(12) United States Patent
Reinert et al.

(10) Patent No.: US 9,101,281 B2
(45) Date of Patent: Aug. 11, 2015

(54) IMD STABILITY MONITOR

(71) Applicant: Medtronic, Inc., Minneapolis, MN (US)

(72) Inventors: Michael A. Reinert, St. Cloud, MN (US); Eric R. Williams, Maple Grove, MN (US); Todd J. Sheldon, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 87 days.

(21) Appl. No.: 13/626,381

(22) Filed: Sep. 25, 2012

(65) Prior Publication Data
US 2013/0079861 A1 Mar. 28, 2013

Related U.S. Application Data

(60) Provisional application No. 61/539,742, filed on Sep. 27, 2011.

(51) Int. Cl.
| | |
|---|---|
| *A61N 1/08* | (2006.01) |
| *A61B 5/053* | (2006.01) |
| *A61B 5/0424* | (2006.01) |
| *A61N 1/375* | (2006.01) |
| *A61N 1/37* | (2006.01) |
| *A61B 5/00* | (2006.01) |
| *A61B 5/042* | (2006.01) |
| *A61B 5/11* | (2006.01) |
| *A61N 1/05* | (2006.01) |
| *A61N 1/365* | (2006.01) |

(52) U.S. Cl.
CPC ............ *A61B 5/0538* (2013.01); *A61B 5/0422* (2013.01); *A61B 5/0424* (2013.01); *A61B 5/11* (2013.01); *A61B 5/686* (2013.01); *A61B 5/6869* (2013.01); *A61N 1/371* (2013.01); *A61N 1/3756* (2013.01); *A61B 5/0031* (2013.01); *A61B 5/6882* (2013.01); *A61B 5/6883* (2013.01); *A61B 2560/0276* (2013.01); *A61B 2560/0468* (2013.01); *A61N 1/0597* (2013.01); *A61N 1/36542* (2013.01); *A61N 2001/083* (2013.01)

(58) Field of Classification Search
None
See application file for complete search history.

(56) References Cited

U.S. PATENT DOCUMENTS

| | | |
|---|---|---|
| 5,117,824 A | 6/1992 | Keimel et al. |
| 5,545,186 A | 8/1996 | Olson et al. |

(Continued)

FOREIGN PATENT DOCUMENTS

WO  2007067231 A1  6/2007

OTHER PUBLICATIONS (PCT/US2012/057408) PCT Notification of Transmittal of the International Search Report and the Written Opinion of the International Searching Authority.

*Primary Examiner* — Kennedy Schaetzle
(74) *Attorney, Agent, or Firm* — Michael C. Soldner

(57) ABSTRACT

Techniques for determining an attachment stability of leadless pacing device (LPD) implanted within a patient are described. For example, the LPD may detect one or more stability metrics from one or more electrodes of the LPD and/or an activity sensor within the LPD. Based on one or more of these stability metrics, e.g., a mechanical motion of the LPD, a stability module within the LPD may determine the attachment stability of the LPD within the patient. If the attachment stability is insufficient to provide efficacious therapy or indicates at least partial dislodgement of the LPD from tissue, the LPD may wirelessly transmit stability information to an external device. In some examples, the LPD may be implanted within a chamber of the heart.

13 Claims, 12 Drawing Sheets

(56) References Cited

U.S. PATENT DOCUMENTS

| | | |
|---|---|---|
| 5,549,652 A | 8/1996 | McClure et al. |
| 5,713,932 A | 2/1998 | Gillberg et al. |
| 5,755,736 A | 5/1998 | Gillberg et al. |
| 6,067,469 A | 5/2000 | Kim et al. |
| 6,445,952 B1 | 9/2002 | Manrodt |
| 6,658,294 B1 * | 12/2003 | Zadeh et al. ............ 607/28 |
| 6,807,439 B2 * | 10/2004 | Edwards et al. ............ 600/420 |
| 6,993,379 B1 | 1/2006 | Kroll et al. |
| 7,200,437 B1 | 4/2007 | Nabutovsky et al. |
| 7,565,195 B1 | 7/2009 | Kroll et al. |
| 7,634,313 B1 | 12/2009 | Kroll et al. |
| 8,700,181 B2 * | 4/2014 | Bornzin et al. ............ 607/126 |
| 2005/0004611 A1 | 1/2005 | Edwards et al. |
| 2005/0096708 A1 | 5/2005 | Seim et al. |
| 2007/0255327 A1 | 11/2007 | Cho et al. |
| 2009/0082828 A1 | 3/2009 | Ostroff |
| 2010/0312131 A1 | 12/2010 | Naware et al. |
| 2010/0312300 A1 | 12/2010 | Ryu et al. |

* cited by examiner

IMD STABILITY MONITOR

This application claims the benefit of U.S. Provisional Application No. 61/539,742, filed Sep. 27, 2011, the entire content of which is incorporated herein by reference.

TECHNICAL FIELD

The invention relates to medical devices, and, more particularly, to implantable medical devices.

BACKGROUND

Cardiac pacing by an artificial pacemaker provides an electrical stimulation to the heart when its own natural pacemaker and/or conduction system fails to provide synchronized atrial and ventricular contractions at rates and intervals sufficient to sustain healthy patient function. Such antibradycardial pacing may provide relief from symptoms, or even life support, for a patient. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a pectoral region of a patient. Therapy parameters are usually interrogated and modified by a programming device outside the body, via a wirelessly-coupled transformer with one inductance within the body and another outside, or via electromagnetic radiation with one antenna within the body and another outside. The generator usually connects to the proximal end of one or more implanted leads, the distal end of which contains one or more electrodes for positioning adjacent to the inside or outside wall of a cardiac chamber. Each of the leads may be secured near or against the cardiac tissue to provide sufficient capture needed to transmit electrical energy to the cardiac tissue.

DETAILED DESCRIPTION

Figure 1:
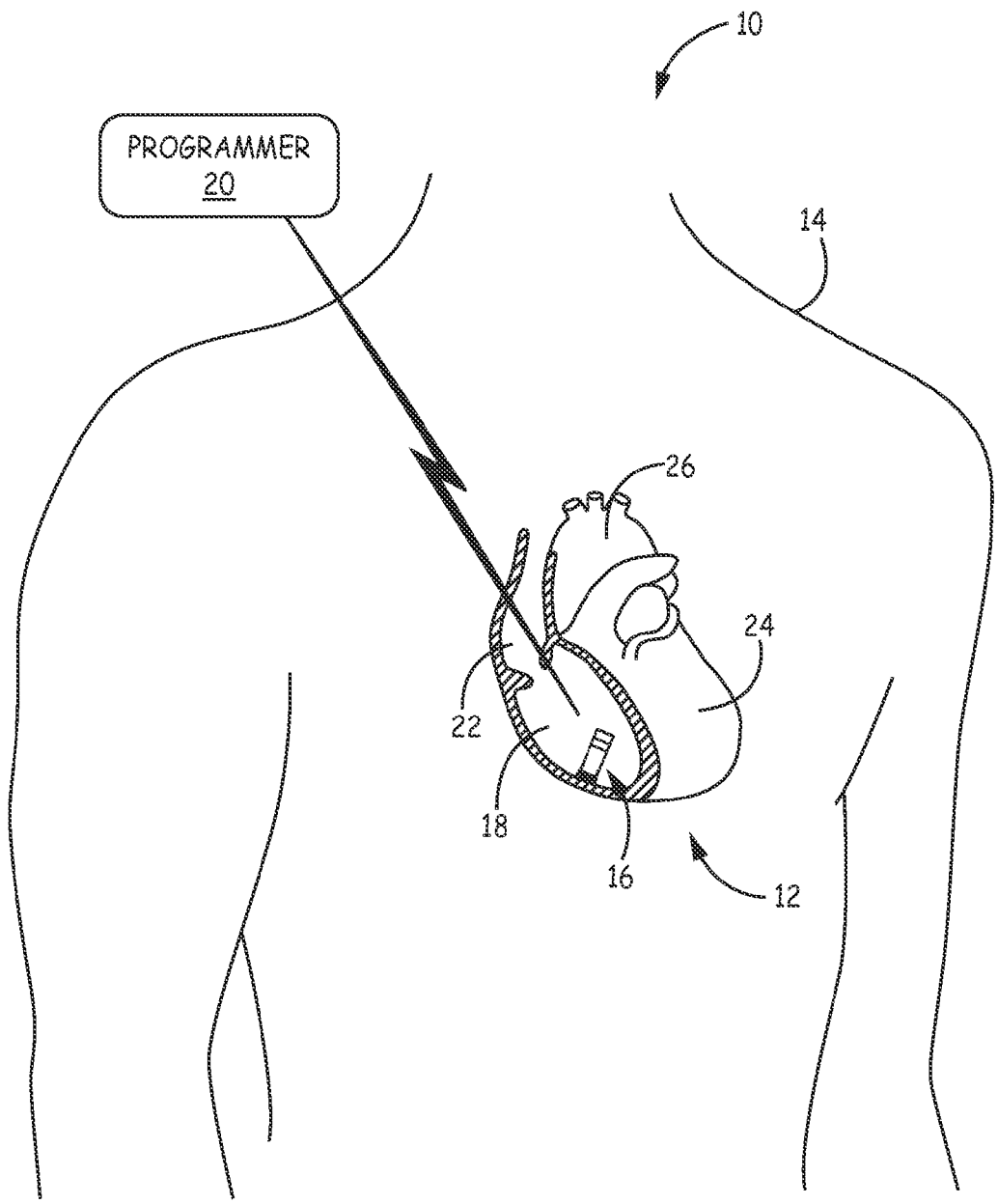
FIG. 1 is a conceptual drawing illustrating an example system that includes a leadless pacing device (LPD) implanted within a cardiac chamber of a patient.

Generally, this disclosure describes various techniques for determining an attachment stability of leadless pacing device (LPD) implanted within a patient. Since an LPD may be an implanted medical device located within a cardiac chamber, dislodgement or even impending detachment may pose an increased health risk to a patient. In addition, LPD dislodgement from the tissue may cause decreased electrode capture and ineffective pacing therapy. By detecting when the LPD may be at least partially dislodged from the target tissue, a clinician may be able to take immediate corrective action. In this manner, the LPD may monitor the stability of the LPD within the patient.

The LPD may detect one or more stability metrics from one or more electrodes of the LPD. In addition, the LPD may also provide an activity sensor within the LPD to detect a stability metric, e.g., based on mechanical motion detected by the activity sensor. In some examples, the activity sensor may include a 3-axis accelerometer. Based on one or more of these stability metrics, a stability module within the LPD may determine the attachment stability of the LPD within the patient. This attachment stability may be determined by comparing the one or more stability metrics to respective specific metric thresholds or to each other. If the attachment stability is insufficient to provide efficacious therapy or indicates at least partial dislodgement of the LPD from tissue, the LPD may wirelessly transmit the stability information to an external device.

In one example, the disclosure describes a method that includes detecting one or more stability metrics with a leadless pacing device implanted within a patient and determining an attachment stability of the leadless pacing device based on the one or more stability metrics.

In another example, the disclosure describes a leadless pacing device including two or more leadless electrodes, a stability module configured to detect one or more stability metrics and determine an attachment stability of the device based on the one or more stability metrics, and a housing that encloses the stability module, wherein the two or more leadless electrodes are disposed on the outside of the housing.

In another example, the disclosure describes a leadless pacing device that includes means for detecting one or more stability metrics with a leadless pacing device implanted within a patient and means for determining an attachment stability of the leadless pacing device based on the one or more stability metrics.

The details of one or more examples are set forth in the accompanying drawings and the description below. Other features, objects, and advantages will be apparent from the description and drawings, and from the claims.

This disclosure describes various techniques for determining an attachment stability of leadless pacing device (LPD) implanted within a patient. An LPD may be a relatively small implantable medical device designed to provide cardiac pacing to a heart of the patient. Instead of utilizing one or more leads that provide electrodes in or near the heart from a remote implant site of the device, the entire LPD may be implanted within a chamber of the heart or on the outside of the heart. In this manner, the LPD may carry the necessary electrodes on the housing of the LPD such that no leads are required by the system. Instead, the LPD may be a fully contained pacemaker within a package that is implantable at the target tissue to be paced.

Since the LPD may be implanted within a chamber of the heart, for example, the LPD may also include one or more fixation mechanisms that secure the LPD to tissue. The fixation mechanisms may penetrate into tissue, adhere to tissue, or otherwise attach the LPD to the tissue. This attachment may be necessary to provide sufficient electrode capture to the tissue and to prevent the LPD from becoming dislodged from the tissue. Since cardiac tissue of the heart is constantly moving, this acceleration may contribute to LPD dislodgement. Insufficient electrode capture may prevent the patient from receiving effective pacing therapy. However, dislodgement of the LPD may pose additional risks such as interference with cardiac muscle contraction, blood flow, valve operation, or even an obstruction to the vasculature downstream from the intended implant site if the LPD exits the heart.

Therefore, this disclosure describes techniques for detecting any dislodgement of the LPD or incomplete capture of the electrode to the target tissue. An attachment stability of the LPD may be determined and used to notify the clinician of any dislodgement and/or insufficient capture at the electrode/tissue interface. If the LPD is dislodged or displaced from tissue, a clinician may take immediate action to recover the LPD and/or reattach the LPD to the tissue of the heart.

The LPD may use one or more techniques or algorithms to determine the attachment stability of the LPD in relation to the target tissue. For example, the LPD may detect one or more stability metrics from one or more electrodes of the LPD. In addition, or alternatively, the LPD may provide an activity sensor within the LPD to detect another stability metric based on mechanical motion of the LPD. This mechanical motion may be generated with a 3-axis accelerometer within the LPD. Based on one or more of these stability metrics, a stability module within the LPD may determine the attachment stability of the LPD within the patient. This attachment stability may be determined by comparing the one or more stability metrics to respective specific metric thresholds or to each other. If the attachment stability is insufficient to provide efficacious therapy or indicates at least partial dislodgement of the LPD from tissue, the LPD may wirelessly transmit stability information to an external device in some examples.

Although the stability techniques described herein are directed to a leadless pacing device (i.e., leadless pacemaker) that is configured to provide electrical stimulation therapy to cardiac tissue, the techniques may also be directed to other leadless implantable medical devices. For example, a leadless neurostimulator may be implanted at a location near a sacral nerve or other nerve of the pelvic floor to provide pain therapy. In another example, a leadless neurostimulator may be implanted within or near a stomach of a patient to manage peristaltic contractions of the gastrointestinal tract. In any case, one or more stability metrics may be used to determine an attachment stability that indicates whether or not, or the degree in which, the device maintains fixation such that there is sufficient tissue contact between one or more electrodes and the target tissue.

FIG. 1 is a conceptual drawing illustrating an example system 10 that includes leadless pacing device (LPD) 16 implanted within heart 12 of patient 14. In the example of FIG. 1, system 10 includes LPD 16 which is coupled to programmer 20. LPD 16 may be, for example, an implantable leadless pacing device (e.g., a pacemaker, cardioverter, and/or defibrillator) that provides electrical signals to heart 12 via electrodes carried on the housing of LPD 16. Patient 14 is ordinarily, but not necessarily a human patient.

In the example of FIG. 1, LPD 16 is implanted within right ventricle 18 of heart 12 to sense electrical activity of heart 12 and/or deliver electrical stimulation to heart 12. LPD 16 may be attached to a wall of the right ventricle 18 via one or more fixation elements that penetrate the tissue. These fixation elements may secure LPD 16 to the cardiac tissue and retain an electrode (e.g., a cathode) in contact with the cardiac tissue. Since LPD 16 includes two or more electrodes carried on the exterior housing of LPD 16, no other leads or structures need to reside in other chambers of heart 12.

In other examples, LPD 16 may be implanted within right atrium 22, left ventricle 24, or the left atrium (not shown). LPD 16 may be attached to a location of heart 12 that is appropriate for propagation of electrical stimulus delivered by LPD 16. However, LPD 16 may be positioned in a variety of locations within heart 12. Typically, LPD 16 may be implanted via an intravenous catheter that is inserted through one or more veins and into the desired right atrium 22 or right ventricle 18. Alternatively, LPD 16 may be attached to an external surface of heart 12 such that LPD 16 is disposed outside of heart 12. For attachment to the external surface of heart 12, a clinician may need to perform an arthroscopic or other minimally invasive surgical technique to implant LPD 16, for example.

Using the electrodes carried on the housing of LPD 16, LPD 16 may be capable sensing intrinsic electrical signals. These intrinsic signals may be electrical signals generated by cardiac muscle and indicative of depolarizations and repolarizations of heart 12 at various times during the cardiac cycle. LPD 16 may generate an electrogram from these cardiac signals that may be used to control pacing of heart 12 and/or identify cardiac events, e.g., ventricle contractions or atrium contractions. LPD 16 may also measure impedances of the carried electrodes and/or determine capture thresholds of those electrodes intended to be in contact with cardiac tissue.

The configurations of electrodes used by LPD 16 for sensing and pacing may be unipolar or bipolar. LPD 16 may detect arrhythmia of heart 12, such as tachycardia or fibrillation of the right atrium 22, left atrium 26 and/or ventricles 18 and 24, and may also provide pacing therapy via the electrodes carried by the housing of LPD 16. In other examples, LPD may provide defibrillation and/or cardioversion therapy via electrodes carried by the housing of LPD 16. In some examples, LPD 16 may be programmed to deliver a stimulation pulses at particular frequencies, based on detected cardiac events, or based on activity of patient 14.

In addition, LPD 16 may monitor the electrical signals of heart 12 for stability metrics stored in LPD 16 and used to determine the attachment stability. LPD 16 may utilize two of any electrodes carried on the housing of LPD 16 to generate electrograms of cardiac activity. In some examples, LPD 16 may also use a cathode and anode carried on the housing of LPD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, LPD 16 may monitor heart rate (night time and day time), heart rate variability, ventricular or atrial intrinsic pacing rates, indicators of blood flow, or other indicators of the ability of heart 12 to pump blood, the progression of heart failure, or other disease states.

LPD 16 may also include an activity sensor to measure or detect mechanical motion of LPD 16. The mechanical motion may be motion with respect to gravity, e.g., changing accelerations of LPD 16, or other structures within patient 14. LPD 16 may monitor these mechanical motions to determine if LPD 16 is still attached to cardiac tissue or if LPD 16 may be at least partially dislodged from the tissue. In one example, LPD 16 may correlate the mechanical motions to the detected cardiac events. If the movement of LPD 16 does not correlate to detected contractions of right ventricle 18, for example, LPD 16 may determine the attachment stability to indicate LPD 16 is at least partially dislodged from the cardiac tissue.

LPD 16 may also communicate with external programmer 20. In some examples, programmer 20 comprises a handheld computing device, computer workstation, or networked computing device. Programmer 20 may include a user interface that receives input from a user. In other examples, the user may also interact with programmer 20 remotely via a networked computing device. The user may interact with programmer 20 to communicate with LPD 16. For example, the user may interact with programmer 20 to send an interrogation request and retrieve stability metrics, the attachment stability, or other stability information from LPD 16. In other examples, LPD 16 may spontaneously initiate communication with programmer 20 to transmit stability information when LPD 16 may be at least partially dislodged from tissue and/or there is an insufficient electrode/tissue interface (e.g., insufficient capture threshold). A user may also interact with programmer 20 to program LPD 16, e.g., select values for operational parameters of LPD 16. Although the user is a physician, technician, surgeon, electrophysiologist, or other healthcare professional, the user may be patient 14 in some examples.

Programmer 20 may also allow the user to define how LPD 16 senses, detects, and manages each of the stability metrics. For example, the user may define the frequency of sampling or the evaluation window used to monitor the stability metrics. In addition, the user may use programmer 20 to set each specific metric threshold that may be used to monitor the status of each stability metric. The specific metric thresholds may be used to determine when each of the stability metrics has reached a magnitude indicative of a lack of capture or at least partial dislodgement of LPD 16. Alternatively, two or more stability metrics may be compared or correlated to determine if each metric is consistent with normal operation of LPD 16. For example, a detected mechanical motion of LPD 16 that does not correlate with the detected cardiac events may indicate dislodgement of LPD 16 because LPD 16 is no longer moving with cardiac muscle contraction.

LPD 16 and programmer 20 may communicate via wireless communication using any techniques known in the art. Examples of communication techniques may include, for example, lower resolution or radiofrequency (RF) telemetry, but other techniques are also contemplated. In some examples, programmer 20 may include a programming head that may be placed proximate to the patient's body near the LPD 16 implant site in order to improve the quality or security of communication between LPD 16 and programmer 20.

As further described herein, LPD 16 may be configured to detect one or more stability metrics within patient 14. LPD 16 may also determine an attachment stability of the LPD based on these one or more stability metrics. LPD 16 may include a stability module that performs this determination of the attachment stability. The attachment stability may be an indication of attachment status between LPD 16 and the target tissue. In this manner, the attachment stability may identify an insufficient electrode/tissue interface for efficacious pacing therapy, e.g., a capture threshold, and an at least partial mechanical dislodgement of LPD 16 from patient tissue. The attachment stability may be provided as a binary variable, e.g., LPD 16 is stable and attached or LPD 16 is unstable and at least partially dislodged from tissue. Alternatively, the attachment stability may be provided with a level or magnitude that indicates a relative severity of dislodgement, e.g., no dislodgement, minimal dislodgement, severe dislodgement, and completely detached.

Example stability metrics may include an electrode impedance, a capture threshold, a cardiac waveform morphology, one or more cardiac events, a pacing threshold, oversensing (e.g., short interval counts), and a mechanical motion of LPD 16. LPD 16 may detect more than one stability metric, but not all stability metrics need be used to determine the attachment stability of LPD 16. In one example, determining the attachment stability may include comparing one or more of the stability metrics to a respective specific metric threshold. Although one stability metric exceeding its specific metric threshold may indicate at least partial dislodgement of LPD 16, a higher number of stability metrics exceeding their respective threshold may indicate a more severe dislodgement of LPD 16 from tissue.

For example, a stability metric may be the orientation of LPD 16 with respect to earth's gravity. LPD 16 may detect the orientation of LPD 16 within patient 14 by using a 3-axis accelerometer. If LPD 16 is oriented outside of a predetermined threshold for the same patient posture, this different orientation may be indicative of at least partial dislodgement of the LPD from the tissue. The predetermined threshold may be an angle between the anticipated gravity vector and the actual vector detected from the accelerometer. LPD 16 may identify the same posture of patient 14 by one or more variables, such as heart rate, breathing rate, activity, patient input, or any other similar variables.

In other examples, LPD 16 may determine the attachment stability by comparing two or more stability metrics to each other. If the metrics do not indicate similar function of LPD 16 or heart 12, LPD 16 may determine that there is an at least partial dislodgement of the LPD from tissue. For example, LPD 16 may compare a mechanical motion (e.g., direction and magnitude of accelerations) detected by the activity sensor of LPD 16 to detected cardiac events and determine the attachment stability to indicate at least partial mechanical dislodgement of the LPD from patient tissue when the mechanical motion does not correlate to the one or more cardiac events. When detected mechanical motions (e.g., accelerations) correlate with cardiac events detected via other metrics, LPD 16 may be determined to be stable or not dislodged from tissue. When the detected mechanical motions have been reduced in magnitude and/or direction as compared to simultaneously detected cardiac contractions (e.g., weaker associations or partial disassociation from each other), LPD 16 may determine that LPD 16 is partially detached from the tissue. When the mechanical motions are not detectable or completely disassociated from cardiac muscle contractions, LPD 16 may determine that the LPD has been completely separated from the tissue or even expelled from the heart. Alternatively, the data from a 3-axis accelerometer or other activity sensor may coupled with one or more stability metrics such as an electrode impedance, oversensing from short interval counts, electrode threshold changes, or the inability to measure a pacing threshold using the electrodes of LPD 16. In this manner, two or more stability metrics may be correlated to ensure LPD 16 is not dislodged from the heart wall.

In some examples, LPD 16 may periodically monitor one stability metric and only detect other stability metrics once the monitored stability metric indicates possible dislodgement of LPD 16. This technique may consume less processing power and extend the battery life of LPD 16. For example, LPD 16 may detect a primary stability metric, e.g., a capture threshold, and determine when the primary stability metric exceeds its respective specific metric threshold. In response to the primary stability metric exceeding its threshold, LPD 16 may then detect a secondary stability metric, e.g., a mechanical motion, and compare the secondary stability metric to its respective specific metric threshold. In this manner, LPD 16 may confirm the initial dislodgement indication with additional stability metrics when necessary.

The value of each stability metric may change based on the severity of the dislodgement of LPD 16. For example, impedance measured between an electrode of LPD and adjacent tissue may decrease as LPD 16 becomes dislodged from tissue. In another example, the pacing threshold may increase with LPD 16 dislodgment. Dislodgement of LPD 16 may also cause a pacing threshold stability metric to become more variable over time. The pacing threshold may be analyzed for variability over two or more measurements. The variability may be a difference between two consecutive measurements or deviation of one or more measurements from an average of previous measurements (e.g., a running average of all pacing thresholds or an average of a most recent subset of pacing thresholds).

In addition, an electrogram measured with an electrode of LPD 16 may change with LPD 16 dislodgement. For example, the cardiac waveform morphology may change with dislodgement. Example morphology changes associated with dislodgment include a decrease in amplitude of the R-wave and/or increase in variability of the R-wave amplitudes in response to dislodgement of LPD 16 from adjacent tissue. This change in the R-wave morphology may be indicative of an increase in heart rate variability, in addition to dislodgement of LPD 16. However, LPD 16 may correlate the R-wave morphology (or other cardiac waveform morphologies) with other stability metrics to differentiate the dislodgement of LPD 16 from a mere increase in heart rate variability.

As described herein, the output of one or more accelerometers within LPD 16 may also be used as a stability metric. The accelerometer may detect accelerations in one axis, two axes, or even three axes. Although a 3-axis accelerometer is generally described herein, a single axis accelerometer may be capable of being used to generate a stability metric. The accelerometer may be used to detect one or more of LPD 16 orientation with respect to patient 14, patient 14 activity, and cardiac accelerations (e.g., cardiac events). The stability metric may include one or more of each of these elements detectable with the accelerometer.

The accelerations detected by LPD 16 may be used to identify the orientation of LPD 16 within patient 14. This orientation may be compared to prior orientations (e.g., the orientation of LPD 16 when initially implanted within patient 14) because the actual orientation of LPD 16 when implanted depends upon patient anatomy and clinician preferences. Since the orientation of LPD 16 within patient 14 may be dependent upon the posture of patient 14, and thus the patient's orientation with respect to gravity, LPD 16 may determine the orientation of LPD 16 for purposes of detecting dislodgment when patient 14 is within a particular posture, or active.

For example, LDP 16 may detect patient activity based on the number and magnitude of components of the signal(s) output by the accelerometer(s) that are within a frequency band associated with patient movement. When LPD 16 detects patient activity, such as walking, running, or general patient activity, the magnitude of the activity is dependent on the alignment of an axis of the accelerometer with the earth's gravity. Greater patient activity may be measured when the accelerometer axis is aligned with the earth's gravity. Therefore, when the magnitude of patient activity remains unchanged, the stability metric may indicate that LPD 16 has not been dislodged. However, if subsequent patient activity with a magnitude different from the magnitude previously detected, this change in magnitude (or the change in vector angle between each detection) may be indicative of the degree in which LPD 16 has been dislodged from the tissue. These changes may also occur during period of patient physical training (e.g. increased patient activity due to a physical fitness program) or detraining (e.g. an illness during which patient activity is decreased), so this patient activity metric may be coupled with other metrics to improve the metric's specificity in some examples.

Figure 9A:
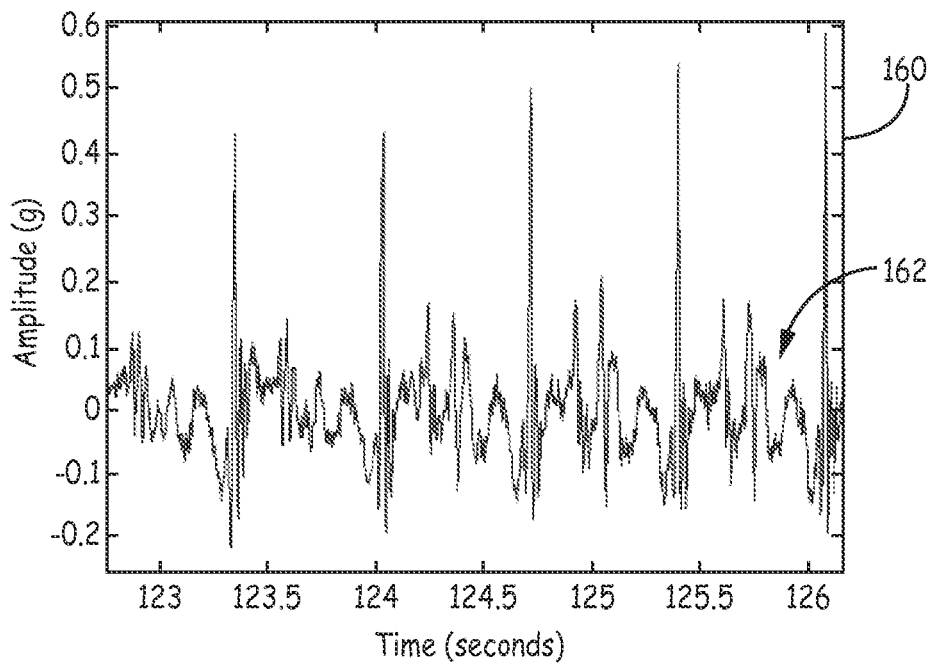
FIGS. 9A and 9B are example graphs of accelerations due to cardiac events and a patient walking, respectively.
Figure 9B:
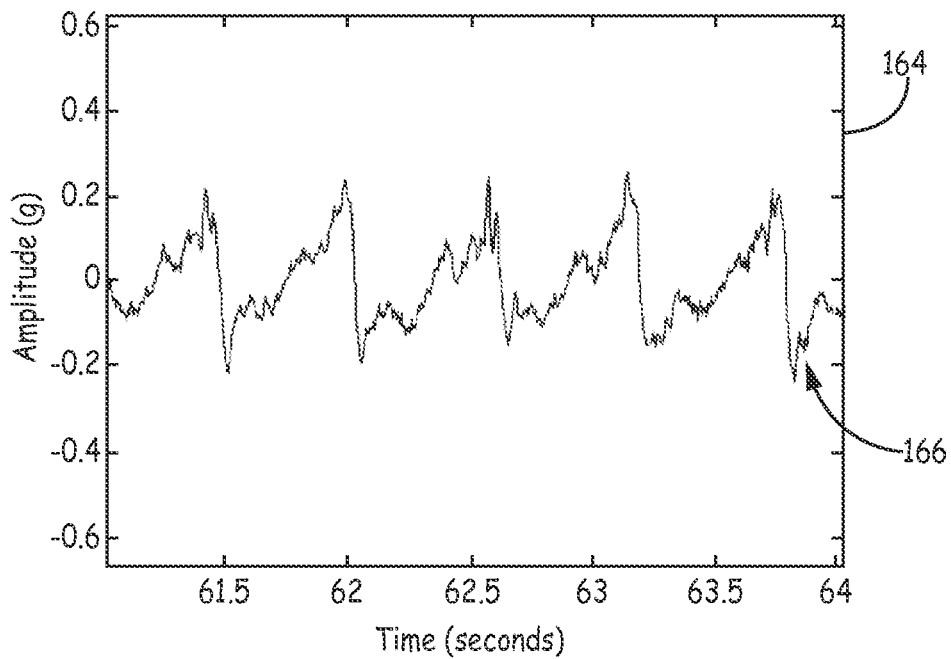

The accelerations detected by LPD 16 may also be used to identify the activity of patient 14. These patient activities may generally occur at a lower frequency than that of cardiac events. For example, the accelerations detected by LPD 16 may be filtered to pass the frequencies generally between 0 Hz and 10 Hz. Since patient activity such as walking and other exercise occurs in the upright position, LPD 16 may monitor the magnitude of the accelerations within the identified activity frequency range. If there is a relatively large change in the magnitude of these vectors from day to day, for example, LPD 16 may determine that the change in magnitude is from dislodgement of LPD 16 instead of an actual change in patient activity. Example patient activity accelerations are illustrated in FIG. 9B.

In addition, the accelerations detected by LPD 16 may be indicative of cardiac events (e.g., accelerations or contractions of a wall of the heart). Generally, the cardiac accelerations occur at higher frequencies than other patient events. For example, cardiac accelerations may be between approximately 10 Hz and 250 Hz. In one example, the cardiac accelerations detected may be the acceleration of the wall that occurs during the first heart sound and associated with the electrical activity of the R-wave. During dislodgement, the morphology of the R-wave acceleration and the timing interval between the acceleration and the electrogram R-wave may change during dislodgement of LPD 16. These changes may be due to poor electrogram sensing and/or poor mechanical coupling of LPD 16 to adjacent tissue. The timing relationship (and any changes therein) between other cardiac accelerations and related electrical events of the electrogram may also be determined Example cardiac accelerations are illustrated in FIG. 9A.

According to these examples, one or more stability metrics may be extracted from a single accelerometer output. For example, LPD 16 may filter out any acceleration changes with a frequency greater than 10 Hz. The remaining accelerations may then be generally representative of patient activity. In another example, LPD 16 may filter out acceleration data with frequencies greater than approximately 1 Hz to identify changes in LPD 16 orientation. In yet another example, LPD 16 may filter out accelerations with frequencies less than approximately 10 Hz and greater than approximately 250 Hz to identify accelerations due to cardiac events such as heart wall contractions. Although LPD 16 may perform filtering and/or other analysis of acceleration data, other computing devices may filter and analyze this data in other examples to determine the attachment stability of LPD 16.

Once LPD 16 determines an attachment stability indicating possible dislodgement of LPD 16, the LPD may generate stability information based the stability metrics and/or the attachment stability. LPD 16 may then wirelessly transmit the stability information from the LPD 16 to programmer 20 or another external device. Communication between LPD 16 may be initiated by programmer 20. However, in other examples, LPD 16 may initiate communication to notify a clinician or other healthcare professional of the dislodgement status of LPD 16. For example, LPD 16 may automatically generate a stability notification and transmit the stability notification to a clinician when the stability information indicates that the pacing therapy is ineffective and/or LPD 16 is at risk for complete detachment from patient tissue.

The attachment stability determined by LPD 16 may provide a proactive technique for identifying any problems with LPD 16 operation. As opposed to leads attached within a heart, dislodgement of LPD 16 may result in a loss of LPD 16 further down the blood stream within patient 14. Therefore, periodic or on demand determination of the attachment stability of LPD 16 may identify possible dislodgement before LPD 16 becomes completely detached from the tissue. In addition, the attachment stability may provide valuable feedback during implantation to determine when LPD 16 is appropriately secured to cardiac tissue.

Figure 2:
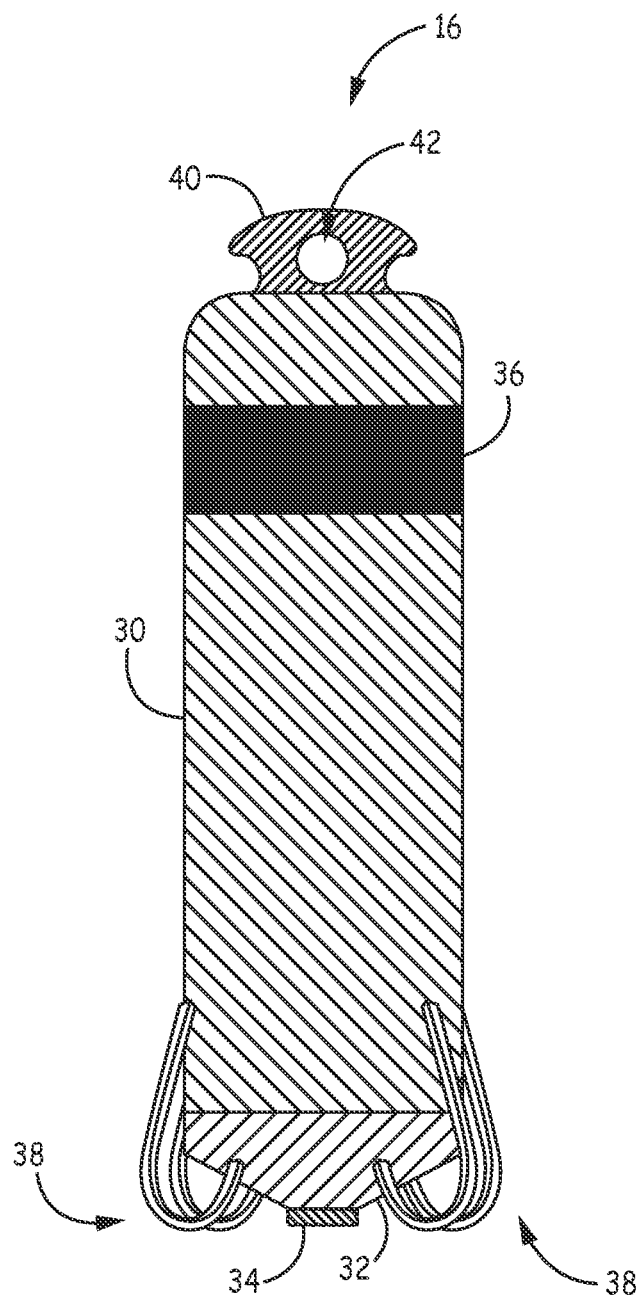
FIG. 2 is a conceptual drawing illustrating an example LPD of FIG. 1.

FIG. 2 is a conceptual drawing illustrating example LPD 16 of FIG. 1. As shown in FIG. 2, LPD 16 includes case 30, cap 32, electrode 34, electrode 36, fixation mechanisms 38, flange 40, and opening 42. Together, case 30 and cap 32 may be considered the housing of LPD 16. In this manner, case 30 and cap 32 may enclose and protect the various electrical components within LPD 16. Case 30 may enclose substantially all of the electrical components, and cap 32 may seal case 30 and create the hermetically sealed housing of LPD 16.

Electrodes 34 and 36 are carried on the housing created by case 30 and cap 32. In this manner, electrodes 34 and 36 may be considered leadless electrodes. In the example of FIG. 2, electrode 34 is disposed on the exterior surface of cap 32. Electrode 34 may be a circular electrode positioned to contact cardiac tissue upon implantation. Electrode 36 may be a ring or cylindrical electrode disposed on the exterior surface of case 30. Both case 30 and cap 32 may be electrically insulating. Electrode 34 may be used as a cathode and electrode 36 may be used as an anode for delivering pacing stimulation therapy. However, electrodes 34 and 36 may be used in any stimulation configuration. In addition, electrodes 34 and 36 may be used to detect intrinsic electrical signals from cardiac muscle. In other examples, LPD 16 may include three or more electrodes, where each electrode may deliver therapy and/or detect intrinsic signals.

Fixation mechanisms 38 may attach LPD 16 to cardiac tissue. Fixation mechanisms 38 may be active fixation tines, screws, clamps, adhesive members, or any other types of attaching a device to tissue. As shown in the example of FIG. 2, fixation mechanisms 38 may be constructed of a memory material that retains a preformed shape. During implantation, fixation mechanisms 38 may be flexed forward to pierce tissue and allowed to flex back towards case 30. In this manner, fixation mechanisms 38 may be embedded within the target tissue. The attachment stability determined by LPD 16 may be used to identify complete attachment during implantation and/or dislodgement of LPD 16 over time. In the event that one or more fixation mechanisms 38 may fail or tear from the tissue, the attachment stability may enable LPD 16 to identify when dislodgement has occurred.

Flange 40 may be provided on one end of case 30 to enable tethering or extraction of LPD 16. For example, a suture or other device may be inserted around flange 40 and/or through opening 42 and attached to tissue. In this manner, flange 40 may provide a secondary attachment structure to tether or retain LPD 16 within heart 12 if fixation mechanisms 38 fail. Flange 40 and/or opening 42 may also be used to extract LPD 16 once the LPD needs to be explanted (or removed) from patient 14 if such action is deemed necessary.

Figure 3A:
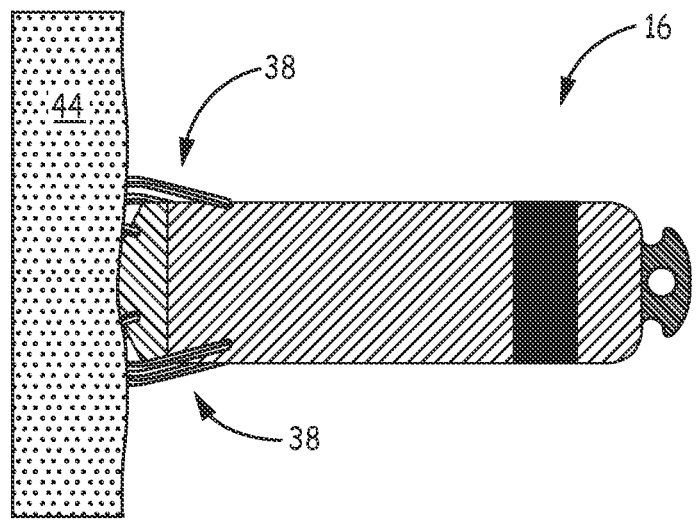
FIGS. 3A and 3B are conceptual drawings that illustrate a fully attached LPD and a dislodged LPD.
Figure 3B:
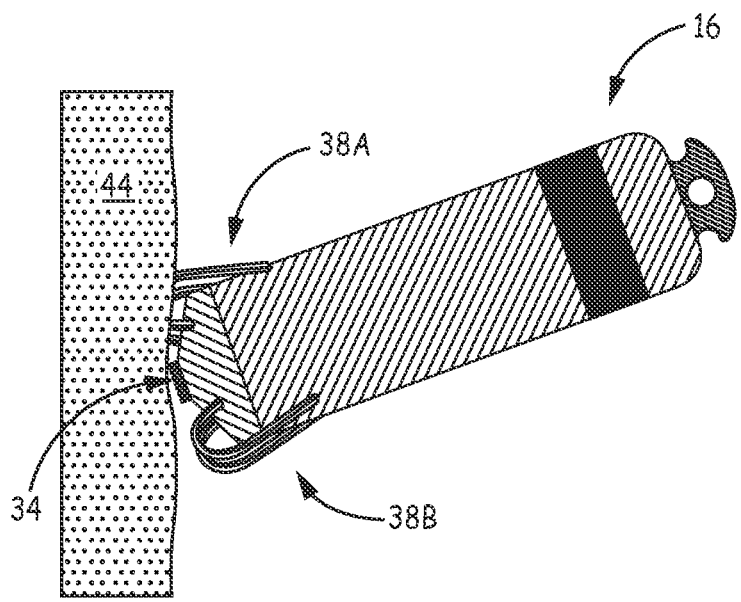

FIGS. 3A and 3B are conceptual drawings that illustrate fully attached LPD 16 and dislodged LPD 16, respectively. As shown in FIG. 3A, LPD 16 is implanted into tissue 44. Tissue 44 may be cardiac tissue, such as a wall of right ventricle 18. Each of fixation mechanisms 38 are engaged into tissue 44 to secure LPD 16 to tissue 44. In addition, fixation mechanism 38 allow electrode 34 (embedded within tissue 44) to make sufficient contact with tissue 44. This contact between electrode 34 and tissue 44 may facilitate electrical capture of cardiac tissue, and the capture threshold may need to be met in order for electrode 34 to transmit the appropriate electrical signals to the cardiac tissue.

LPD 16 is secured to tissue 44 and not dislodged from the tissue in FIG. 3A. Therefore, FIG. 3A may indicate a fully operational implant position of LPD 16 against tissue 44. During the implantation process, LPD 16 may transmit an attachment stability and/or individual stability metrics to programmer 20 to indicate when LPD 16 is securely attached to tissue 44.

In contrast, FIG. 3B illustrates an example condition in which LPD 16 is partially dislodged from tissue 44. Fixation mechanisms 38B have become detached from tissue 44 and other fixation mechanisms 38A remain attached to tissue 44. In other examples, any number of fixation mechanisms detached from tissue 44 may cause at least partial dislodgement. However, in this configuration, electrode 34 may also be intermittently or permanently decoupled from tissue 44. The capture threshold of electrode 34 may not be met, the electrode impedance may be increased, and LPD 16 may no longer be able to accurately detect cardiac events from intrinsic signals.

In addition, a partially dislodged LPD 16 may detect mechanical motion that does not correlate to the movement of the chamber wall indicated by tissue 44. As tissue 44 moves during contractions and relaxations, LPD 16 may move erratically due to chamber wall movement and surrounding blood flow. In this manner, the mechanical motion or accelerations detected by an activity sensor within LPD 16 may indicate that dislodgement has occurred. Once LPD 16 becomes at least partially dislodged from tissue 44, the clinician may need to surgically remove or reattach LPD 16. As mentioned above, complete dislodgement of LPD 16 from tissue 44 from result in LPD 16 moving to a different area of heart 12 or even through the vasculature if no other attachment mechanism prevents LPD 16 from moving.

In an example in which LPD 16 is configured as a neurostimulator, FIGS. 3A and 3B may similarly illustrate sufficient and insufficient electrical contact between an electrode and the target tissue, respectively. Even for neurostimulators, it may be beneficial to monitor the stability or dislodgement of the device as an indication of sufficient electrical contact or capture between electrodes and tissue. For example, FIG. 3A may illustrate a sufficient electrical contact made between tissue 44 and electrode 34 in a neurostimulator, e.g., an implantable medical device implanted to stimulate nerves or muscle involved in controlling the stomach, intestinal motility, bladder, or any other tissue or organ.

Figure 4:
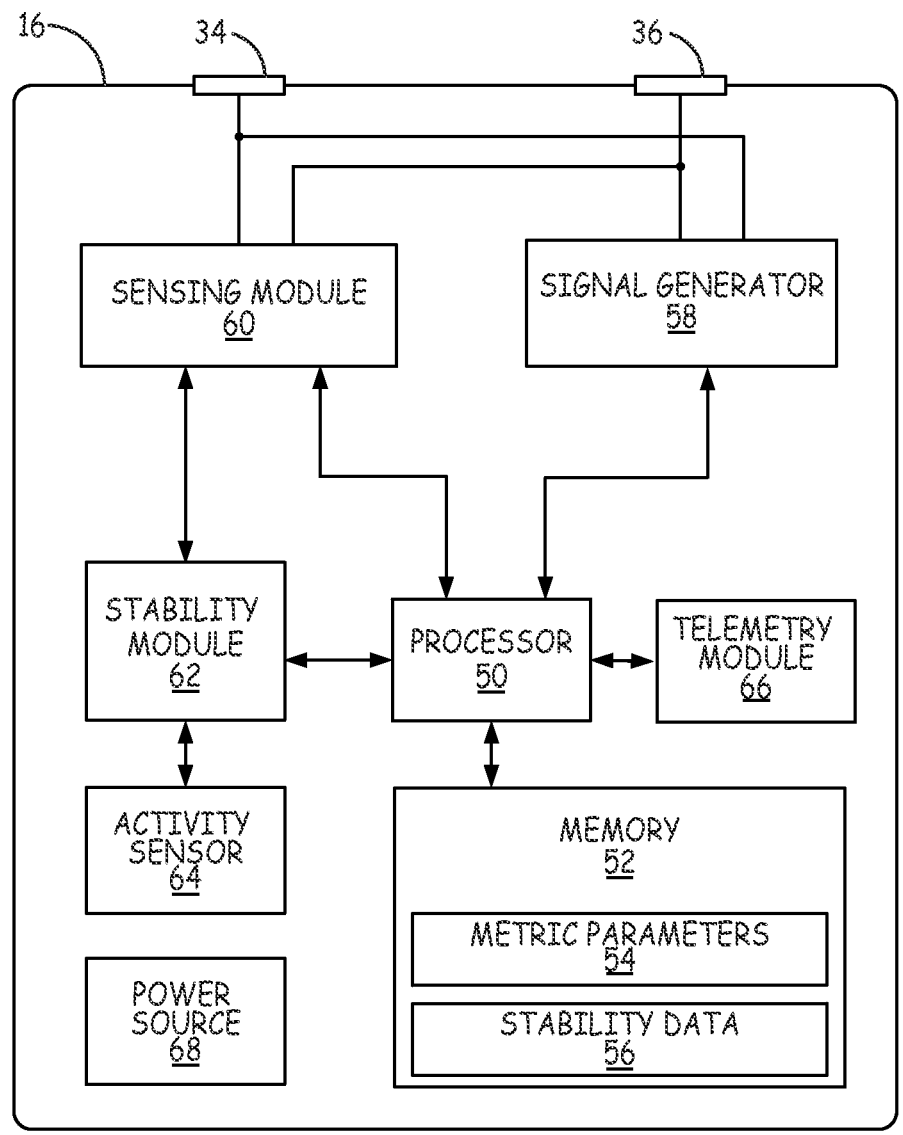
FIG. 4 is a functional block diagram illustrating an example configuration of the LPD of FIG. 1.

FIG. 4 is a functional block diagram illustrating an example configuration of LPD 16. In the illustrated example, LPD 16 includes a processor 50, memory 52, stability module 62, signal generator 58, sensing module 60, telemetry module 66, and power source 68. Memory 52 includes computer-readable instructions that, when executed by processor 50, cause LPD 16 and processor 50 to perform various functions attributed to LPD 16 and processor 50 herein. Memory 52 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 50 may include any one or more of a microprocessor, a controller, a digital signal processor (DSP), an application specific integrated circuit (ASIC), a field-programmable gate array (FPGA), or equivalent discrete or analog logic circuitry. In some examples, processor 50 may include multiple components, such as any combination of one or more microprocessors, one or more controllers, one or more DSPs, one or more ASICs, or one or more FPGAs, as well as other discrete or integrated logic circuitry. The functions attributed to processor 50 herein may be embodied as software, firmware, hardware or any combination thereof.

Processor 50 controls signal generator 58 to deliver stimulation therapy to heart 12 according to a therapy parameters, which may be stored in memory 52. For example, processor 50 may control signal generator 58 to deliver electrical pulses with the amplitudes, pulse widths, frequency, or electrode polarities specified by the therapy parameters. In this manner, signal generator 58 may deliver pacing pulses to heart 12 via electrodes 34 and 36. Although LPD 16 may only include two electrodes, e.g., electrodes 34 and 36, LPD 16 may utilize three or more electrodes. LPD 16 may use any combination of electrodes to deliver therapy and/or detect electrical signals from patient 14.

Signal generator 58 is electrically coupled to electrodes 34 and 36 carried on the housing of LPD 16. In the illustrated example, signal generator 58 is configured to generate and deliver electrical stimulation therapy to heart 12. For example, signal generator 58 may deliver pacing pulses to a portion of cardiac muscle within heart 12 via electrodes 34 and 36. In some examples, signal generator 58 may deliver pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 58 may also include circuitry for measuring the capture threshold of one or both electrodes 34 and 36. The capture threshold may indicate the voltage necessary to induce depolarization of the surrounding cardiac muscle. For example, signal generator 58 may measure the voltage of pacing signals needed to induce ventricular contractions. In examples in which LPD 16 includes more than two electrodes, signal generator 58 may include a switch module and processor 50 may use the switch module to select, e.g., via a data/address bus, which of the available electrodes are used to deliver pacing pulses. The switch module may include a switch array, switch matrix, multiplexer, or any other type of switching device suitable to selectively couple stimulation energy to selected electrodes.

Electrical sensing module 60 monitors signals from at least one of electrodes 34 and 36 in order to monitor electrical activity of heart 12, impedance, or other electrical phenomenon. Sensing may be done to determine heart rates or heart rate variability, or to detect arrhythmias or other electrical signals. Sensing module 60 may also include a switch module to select which of the available electrodes are used to sense the heart activity, depending upon which electrode combination, or electrode vector, is used in the current sensing configuration. In examples with several electrodes, processor 50 may select the electrodes that function as sense electrodes, i.e., select the sensing configuration, via the switch module within sensing module 60. Sensing module 60 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 50, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 50 may control the functionality of sensing module 60 by providing signals via a data/address bus.

Processor 50 may include a timing and control module, which may be embodied as hardware, firmware, software, or any combination thereof. The timing and control module may comprise a dedicated hardware circuit, such as an ASIC, separate from other processor 50 components, such as a microprocessor, or a software module executed by a component of processor 50, which may be a microprocessor or ASIC. The timing and control module may implement programmable counters. If LPD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR and other modes of pacing.

Intervals defined by the timing and control module within processor 50 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 60 for a time interval during and after delivery of electrical stimulation to heart 12. The durations of these intervals may be determined by processor 50 in response to stored data in memory 52. The timing and control module of processor 50 may also determine the amplitude of the cardiac pacing pulses.

Interval counters implemented by the timing and control module of processor 50 may be reset upon sensing of R-waves and P-waves with detection channels of sensing module 60. In examples in which LPD 16 provides pacing, signal generator 58 may include pacer output circuits that are coupled to electrodes 34 and 46, for example, appropriate for delivery of a bipolar or unipolar pacing pulse to one of the chambers of heart 12. In such examples, processor 50 may reset the interval counters upon the generation of pacing pulses by signal generator 58, and thereby control the basic timing of cardiac pacing functions, including anti-tachyarrhythmia pacing.

The value of the count present in the interval counters when reset by sensed R-waves and P-waves may be used by processor 50 to measure the durations of R-R intervals, P-P intervals, P-R intervals and R-P intervals, which are measurements that may be stored in memory 52. Processor 50 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 52 may be configured as a plurality of recirculating buffers, capable of holding series of measured intervals, which may be analyzed by processor 50 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 50 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 50 in other examples.

In some examples, processor 50 may determine that tachyarrhythmia has occurred by identification of shortened R-R (or P-P) interval lengths. Generally, processor 50 detects tachycardia when the interval length falls below 220 milliseconds (ms) and fibrillation when the interval length falls below 180 ms. These interval lengths are merely examples, and a user may define the interval lengths as desired, which may then be stored within memory 52. This interval length may need to be detected for a certain number of consecutive cycles, for a certain percentage of cycles within a running window, or a running average for a certain number of cardiac cycles, as examples.

In the event that processor 50 detects an atrial or ventricular tachyarrhythmia based on signals from sensing module 60, and an anti-tachyarrhythmia pacing regimen is desired, timing intervals for controlling the generation of anti-tachyarrhythmia pacing therapies by signal generator 58 may be loaded by processor 50 into the timing and control module to control the operation of the escape interval counters therein and to define refractory periods during which detection of R-waves and P-waves is ineffective to restart the escape interval counters for the an anti-tachyarrhythmia pacing.

In addition to detecting and identifying specific types of cardiac rhythms (types of cardiac events), sensing module 60 may also sample the detected intrinsic signals to generate an electrogram or other time-based indication of cardiac events. In some examples, an electrogram of cardiac activity may be used to determine the attachment stability of LPD 16. Processor 50 may determine if the electrogram morphology indicates that LPD 16 may be dislodged or a level of dislodgement. The detected signal morphology may be compared to a baseline or other threshold to indicate if the cardiac activity appears to be abnormal. If abnormal activity does not appear to correlate with typical abnormal rhythms, processor 50 may determine that LPD 16 no longer has a stable attachment. The electrogram morphology may be indicative of an evoked response anomaly that indicates cardiac tissue is reacting differently to pacing pulses than would be expected. This unexpected result may be indicative that LPD 16 has been at least partially dislodged from tissue. For example, processor 50 may determine if an R-wave amplitude of the morphology has changed with respect to previously detected R-waves. Lower amplitude R-waves may indicate that an electrode is becoming detached from the tissue. This change in morphology may be compared with mechanical motion, for example, to detect any dislodgement of LPD 16.

Sensing module 60 may also measure electrode impedance of electrodes 34 and 36. If the impedance of electrode 34, for example, increases above a predetermined threshold or rolling average threshold, stability module 62 may determine that LPD 16 is at least partially dislodged from tissue. In a partially dislodged state, the impedance measured by sensing module 60 may vary widely depending on the contact between tissue and electrode 34.

Memory 52 may be configured to store a variety of operational parameters, therapy parameters, sensed and detected data, and any other information related to the therapy and treatment of patient 14. In the example of FIG. 4, memory 52 also includes metric parameters 54 and stability data 56. Metric parameters 54 may include all of the parameters and instructions required by processor 50 and stability module 62 to sense and detect each of the stability metrics used to determine the attachment stability of LPD 16. For example, metric parameters 54 may include instructions on how and when to detect each of the stability metrics and even the values of respective specific metric thresholds for each of the stability metrics. Stability data 56 may store all of the data generated from the sensing and detecting of each stability metric. In this manner, memory 52 may store a plurality of automatically detected stability metrics as the data required to determine an attachment stability of LPD 16 during implantation and/or during operation of LPD 16 within patient 14.

Metric parameters 54 may include definitions of each of the stability metrics automatically sensed or measured by stability module 62. These definitions may include instructions regarding what electrodes or sensors to use in the detection of each metric, the sample rate, calibration schemes, metric specific thresholds, and any other related information. In one example, the stability metrics for which metric parameters are stored as metric parameters 54 and may include an electrode impedance, a capture threshold, a cardiac waveform morphology, sensing performance, one or more cardiac events, and/or a mechanical motion of LPD 16. These stability metrics may utilize any one or more of sensing module 60, signal generator 58, stability module 62, activity sensor 64, or processor 50.

Stability module 62 may instruct the detection of one or more of the stability metrics at a predetermined frequency or in response to certain events. In one example, each of the stability metrics used to determine the attachment stability may be detected once every hour. In other examples, the frequency of detection for each stability metric may occur as infrequently has once a day or longer. Alternatively, each of the stability metrics may be detected continuously for up to date monitoring of the attachment stability. In general, the stability metrics may be detected between once a minute and once a week. In addition, some stability metrics may be detected at different frequencies than other stability metrics. Stability module 62 may determine the attachment stability upon the detection of a new stability metric or at a predetermined frequency in a range similar to the frequency of detection for the stability metrics. Furthermore, the stability metrics may be detected, or the attachment stability determined, in response to a request from an external computing device (e.g., programmer 20).

Metric parameters 54 may also store a metric specific threshold for each of the stability metrics automatically detected by stability module 62. Specific metric thresholds may be predetermined and held constant over the entire monitoring of patient 14. In some examples, however, metric thresholds may be modified by a user during therapy or processor 50 may automatically modify one or more specific metric thresholds to compensate for certain patient conditions. For example, a capture threshold may be changed over the course of monitoring if the normal or baseline capture threshold has migrated during therapy. In this manner, the specific metric thresholds may be based on a rolling average or weighted average of more recent stability metric values to compensate for changes to implanted hardware and/or the health of patient 14.

Stability module 62 may be configured to utilize one or more stability metrics to generate an attachment stability of LPD 16. The attachment stability may identify an insufficient electrode/tissue interface for efficacious pacing therapy and/or an at least partial mechanical dislodgement of LPD 16 from patient tissue. In other words, the attachment stability may be a value, level, severity indication, or attachment status of LPD 16 within patient 14. For example, the attachment stability may provide a binary "secure" or "unsecure" status. When the attachment stability indicates that LPD 16 is unsecure, the clinician may choose to take surgical intervention actions to either remove or reattach LPD 16. Alternatively, the attachment stability may provide an indication of various levels of dislodgement of LPD 16. For example, the attachment stability may be provided on a scale of zero to five, where zero indicates that LPD 16 is fully attached to the tissue, five indicates full detachment of LPD 16 from tissue, and one through four indicates increasing severities of LPD dislodgement. In this manner, stability module 62 may be able to use the detected stability metrics to provide detailed information about the attachment stability of LPD 16 within patient 16.

Stability module 62 may determine the attachment stability using various different techniques. In one example, stability module 62 may compare one or more stability metrics to respective specific metric thresholds. If the stability metric does not exceed the specific metric threshold, LPD 16 may still be securely attached to tissue. Each stability metric may include a single threshold to indicate whether or not LPD 16 is attached to tissue, or each stability metric may include two or more thresholds to provide varying levels of dislodgement. For example, the capture threshold may indicate dislodgement once the voltage of the electrode exceeds the voltage of the specific metric threshold. Alternatively, the capture threshold may indicate increasing magnitudes of dislodgement as the voltage of the capture threshold exceeds subsequent specific metric thresholds. These single or multiple metric thresholds may be provided for each of the stability metrics.

It is also noted that exceeding a metric threshold does not require that the detected value of the stability metric becomes greater than the magnitude of the threshold. For some stability metrics, exceeding the metric threshold may occur when the value of the stability metric drops below the metric threshold. Therefore, each threshold may be merely a boundary that indicates whether or not LPD 16 is dislodged from tissue any time that the metric threshold is crossed.

In other examples, stability module 62 may determine the attachment stability of LPD 16 by comparing two of the stability metrics to each other. Each of the stability metrics may indicate a change in one aspect of LPD 16 function, position, or relation to tissue. If one of the stability metrics changes and another stability metric does not correspondingly change, then stability module 62 may determine that there has been some level of dislodgement. For example, stability module 62 may determine at least partial attachment dislodgement of LPD by comparing the mechanical motion of LPD 16 to one or more cardiac events and determining when the mechanical motion does not correlate to the one or more cardiac events. Activity sensor 64 may detect a mechanical motion of LPD 16f with respect to gravity, for example. Since LPD 16 may be attached to a wall of heart 12, the motion or acceleration of LPD 16 changes as the cardiac muscle of the wall contracts and relaxes. Therefore, if the mechanical motion of LPD 16 does not indicate a heart contraction when a cardiac event of a pacing pulse or intrinsic ventricular contraction occurs, the stability module 62 may determine that LPD 16 is at least partially detached from the tissue. As the mechanical motion becomes increasingly disconnected from cardiac events, the severity of dislodgement may also be indicated. In other examples, other stability metrics may be compared, e.g., capture threshold and mechanical motion or capture threshold and cardiac events.

In another example, stability module 62 may only detect a limited number of the stability metrics on a regular basis and detect other stability metrics in response to the regularly detected metrics indicating possible dislodgment. This responsive detection may be used to save power by monitoring one or two stability metrics and only detecting other stability metrics to confirm potential dislodgement. For example, stability module 62 may regularly monitor the capture threshold of electrode 34 and determine the attachment dislodgement based on the capture threshold. If the capture threshold begins to exceed the specific metric threshold, this out of range capture threshold may indicate at least partial dislodgement of LPD 16. To confirm the dislodgement and/or identify the severity of the dislodgement, stability module 62 may detect other stability metrics and compare these metrics to their thresholds and/or other metrics. In this manner, stability module 62 may selectively detect stability metrics to conserve power of LPD 16.

Stability module 62 may transmit the determined attachment stability of LPD 16 on a periodic basis, in response to a request from an external device, or upon connection with an external device, e.g., programmer 20. In other examples, stability module 62 may initiate transmission of the attachment stability when the attachment stability indicates at least partial dislodgement of LPD 16. Stability module 62 may trigger transmission from telemetry module 66 as necessary to information a clinician of potential dislodgement that may be detrimental to the health of patient 14. In some examples, stability module 62 may automatically detect each of the stability metrics and store them within stability data 56 for later transmission. Stability module 62 may be any type of hardware (e.g., a specialized circuit or processor) or a software module executed by a processor (e.g., processor 50).

Stability data 56 is a portion of memory 52 that may store some or all of the stability metric data that is sensed and detected by stability module 62. Stability data 56 may store the data for each metric on a rolling basis and delete old data as necessary or only for a predetermined period of time, e.g., an evaluation window. Processor 50 may access stability data when necessary to retrieve and transmit patient stability data and/or generate the attachment stability. Although metric parameters 54 and/or stability data 56 may consist of separate physical memories, these components may simply be an allocated portion of the greater memory 52.

It is noted that functions attributed to stability module 62 herein may be embodied as software, firmware, hardware or any combination thereof. In some examples, stability module 62 may at least partially be a software process executed by processor 50. Stability module 62 may sense or detect any of the stability metrics used as a basis for generating and determining the attachment stability of LPD 16.

Activity sensor 64 may be contained within the housing of LPD 16 and include one or more accelerometers or other devices capable of detecting motion and/or position of LPD 16. For example, activity sensor 64 may include a 3-axis accelerometer that is configured to detect accelerations in any direction in space. Specifically, the 3-axis accelerator may be used to detect LPD 16 instability or detachment by identifying weakened accelerations corresponding to cardiac contractions, identifying a different orientation with respect to gravity, or determining whether the accelerometer data is consistent with electrical measurements (e.g., electrode impedance, short interval counts associated with oversensing, threshold changes, or the inability to measure a pacing threshold.) In the example of varying LPD 16 orientation, LPD 16 may monitor heart rate or other patient data to identify the posture or patient 14.

Since LPD 16 may be attached to a wall of heart 12, the mechanical motions and/or accelerations detected by activity sensor 54 may correspond to cardiac events when LPD 16 is sufficiently attached. However, dislodgement of LPD 16 from the heart wall may lead to accelerations also influenced by blood flow or contacts with heart walls than only wall motion. In this manner, monitoring the output of activity sensor 64 may be used to identify the attachment stability of LPD 16. In some examples, the mechanical motion from activity sensor 64 stored over time may be reviewed to identify any abnormalities in mechanical motion of LPD 16 due to certain times of day or other events that may indicate potential dislodgement of LPD 16. In other examples, activity sensor 64 may be configured to detect an activity level and/or orientation of patient 14 with respect to gravity.

In some examples, the specific metric thresholds used to generate the attachment stability may change over time, e.g., may either be modified by a user or automatically changed based on other patient conditions. Telemetry module 66 may receive commands from programmer 20, for example, to modify one or more metric parameters 54 (e.g., metric creation instructions or specific metric thresholds). Alternatively, processor 50 may automatically adjust a specific metric threshold if certain conditions are present in patient 14. For example, the threshold may be adjusted if patient 14 is experiencing certain arrhythmias or normal electrograms change in a manner that requires a change in the threshold.

In some examples, programmer 20, a computing device, or a server may thus include a metric detection module similar to stability module 62 described herein. LPD 16 may continue to collect stability metric values and process the values for transmission. In addition, processor 50 may transmit the specific metric thresholds with the stability metric data so that any external device may determine the attachment stability of patient 14.

As described above, processor 50 may provide an alert to a user, e.g., of programmer 20, regarding the data from any stability metric and/or the attachment stability. In one example, processor 50 may provide an alert with the attachment stability when programmer 20 or another device communicates with LPD 16. This communication may be in the form of an interrogation request that is sent to LPD 16. In other examples, processor 50 may push an alert to programmer 20 or another device whenever the attachment stability indicates LPD 16 is at least partially dislodged via transmission by telemetry module 66.

Telemetry module 66 includes any suitable hardware, firmware, software or any combination thereof for communicating with another device, such as programmer 20 (FIG. 1). As described herein, telemetry module 66 may transmit stability information (e.g., stability metrics, the attachment stability, or any other related data). Under the control of processor 50, telemetry module 66 may receive downlink telemetry from and send uplink telemetry to programmer 20 with the aid of an antenna, which may be internal and/or external. Processor 50 may provide the data to be uplinked to programmer 20 and the control signals for the telemetry circuit within telemetry module 66, e.g., via an address/data bus. In some examples, telemetry module 66 may provide received data to processor 50 via a multiplexer.

In some examples, LPD 16 may signal programmer 20 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., stability metric data in the form of an attachment stability, to the user. LPD 16 may spontaneously transmit the diagnostic information to the network or in response to an interrogation request from a user.

Power source 68 may be any type of device that is configured to hold a charge to operate the circuitry of LPD 16. Power source 68 may be provided as a rechargeable or non-rechargeable battery. In other example, power source 68 may incorporate an energy scavenging system that stores electrical energy from movement of LPD 16 within patient 14.

Figure 5:
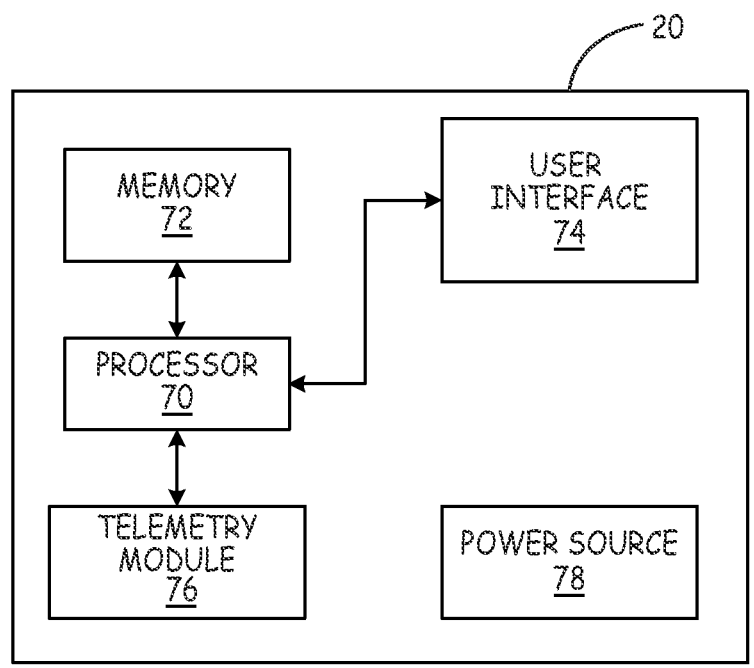
FIG. 5 is a functional block diagram illustrating an example configuration of an external programmer that facilitates user communication with the LPD.

FIG. 5 is a functional block diagram illustrating an example configuration of external programmer 20 that facilitates user communication with LPD 16. As shown in FIG. 4, programmer 20 may include a processor 70, memory 72, user interface 74, telemetry module 76, and power source 78. Programmer 20 may be a dedicated hardware device with dedicated software for programming of LPD 16. Alternatively, programmer 20 may be an off-the-shelf computing device running an application that enables programmer 20 to program LPD 16.

A user may use programmer 20 to configure the operational parameters of and retrieve data from LPD 16 (FIG. 1). The clinician may interact with programmer 20 via user interface 74, which may include display to present graphical user interface to a user, and a keypad or another mechanism for receiving input from a user. In addition, the user may receive an alert or notification from LPD 16 indicating the attachment stability of LPD 16 and/or stability metrics via programmer 20.

Processor 70 can take the form one or more microprocessors, DSPs, ASICs, FPGAs, programmable logic circuitry, or the like, and the functions attributed to processor 70 herein may be embodied as hardware, firmware, software or any combination thereof. Memory 72 may store instructions that cause processor 70 to provide the functionality ascribed to programmer 20 herein, and information used by processor 70 to provide the functionality ascribed to programmer 20 herein. Memory 72 may include any fixed or removable magnetic, optical, or electrical media, such as RAM, ROM, CD-ROM, hard or floppy magnetic disks, EEPROM, or the like. Memory 72 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with LPD 16, such as using RF communication or proximal inductive interaction. This wireless communication is possible through the use of telemetry module 76, which may be coupled to an internal antenna or an external antenna. An external antenna that is coupled to programmer 20 may correspond to the programming head that may be placed over heart 12, as described above with reference to FIG. 1. Telemetry module 76 may be similar to telemetry module 66 of LPD 16 (FIG. 4).

Telemetry module 76 may also be configured to communicate with another computing device via wireless communication techniques, or direct communication through a wired connection. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. An additional computing device in communication with programmer 20 may be a networked device such as a server capable of processing information retrieved from LPD 16.

In this manner, telemetry module 76 may transmit an interrogation request to telemetry module 66 of LPD 16. Accordingly, telemetry module 76 may receive the attachment stability indication from LPD 16. In some examples, an alert of at least partially dislodged LPD 16 may be automatically transmitted, or pushed, by LPD 16. In addition, the alert may be a notification to a healthcare professional, e.g., a clinician or nurse, of a need for surgical intervention to remedy the dislodgement. This alert may be an instruction to patient 14 to seek medical treatment. In response to receiving the alert, user interface 74 may present the alert to the healthcare professional regarding the risk level or present an instruction to patient 14 to seek medical treatment.

In some examples, user interface 74 may present the attachment stability to the user indicating the level of dislodgement of LPD 16 within patient 14. In other examples, user interface 74 may present one or more stability metrics that may or may not have been used to determine the attachment stability of LPD 16. User interface 74 may allow a clinician to further investigate the severity of LPD 16 dislodgement using one or more stability metrics. In addition, the user may interact with user interface 74 to select different techniques and/or specific metric thresholds for LPD 16 to determine the attachment stability. Telemetry module 76 may then transmit the updated instructions to LPD 16.

Upon receiving the alert via user interface 74, the user may also interact with user interface 74 to cancel the alert, forward the alert, retrieve data regarding the attachment stability, modify the specific metric thresholds used to determine the attachment stability, or conduct any other action related to the treatment of patient 14. In some examples, the clinician may be able to review raw data (e.g., values used to detect each stability metric) to diagnose any other problems with patient 14 or LPD 16. User interface 74 may also allow the user to specify the type and timing of alerts based upon the severity or criticality of the attachment stability.

In some examples, processor 70 of programmer 20 and/or one or more processors of one or more networked computers may perform all or a portion of the techniques described herein with respect to processor 50, metric stability module 62 and LPD 16. For example, processor 70 or a stability module 62 within programmer 20 may analyze stability metrics to detect those metrics exceeding thresholds and to generate the attachment stability.

Figure 6:
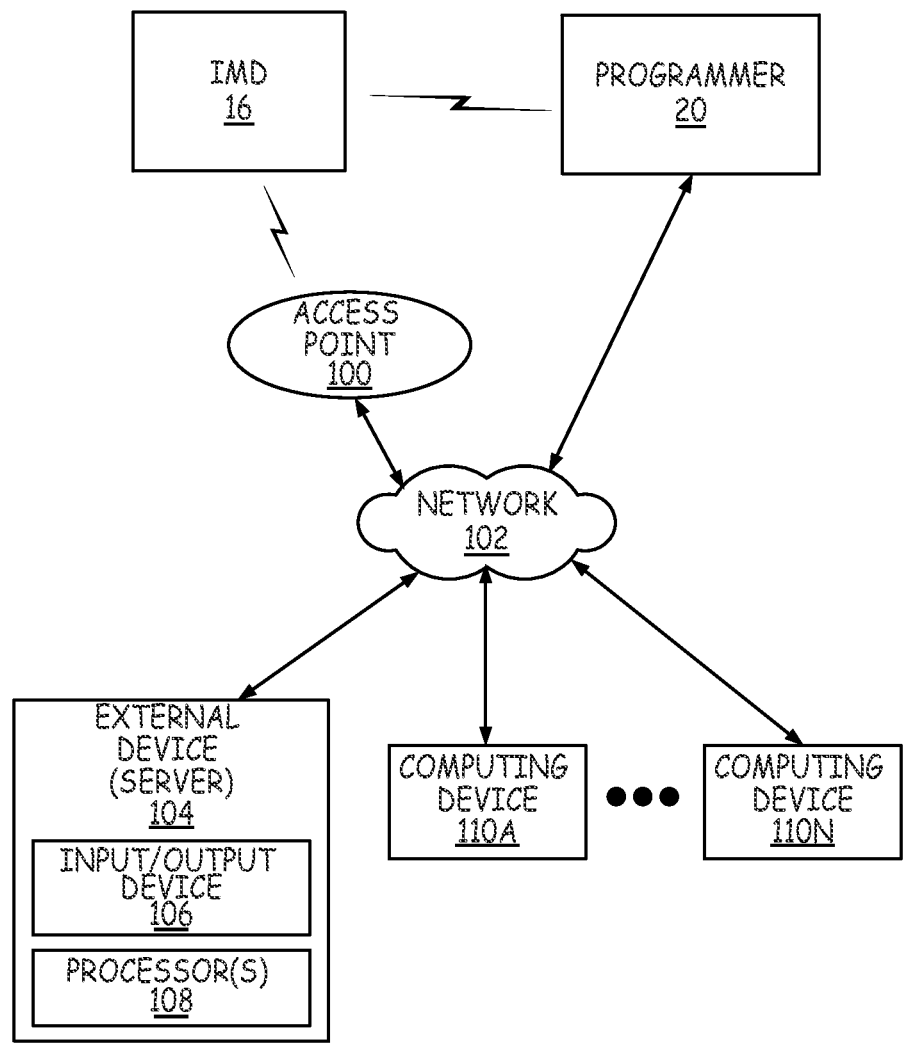
FIG. 6 is a block diagram illustrating an example system that includes an external device, such as a server, and one or more computing devices that are coupled to the LPD and programmer shown in FIG. 1 via a network.

FIG. 6 is a block diagram illustrating an example system that includes an external device, such as a server 104, and one or more computing devices 110A-110N, that are coupled to the LPD 16 and programmer 20 shown in FIG. 1 via a network 102. Network 102 may be generally used to transmit the attachment stability of LPD 16 (or stability metrics) from a remote LPD 16 to another external computing device. In this example, LPD 16 may use its telemetry module 66 to communicate with programmer 20 via a first wireless connection, and to communication with an access point 100 via a second wireless connection. In the example of FIG. 6, access point 100, programmer 20, server 104, and computing devices 110A-110N are interconnected, and able to communicate with each other, through network 102. In some cases, one or more of access point 100, programmer 20, server 104, and computing devices 110A-110N may be coupled to network 102 through one or more wireless connections. LPD 16, programmer 20, server 104, and computing devices 110A-110N may each comprise one or more processors, such as one or more microprocessors, DSPs, ASICs, FPGAs, programmable logic circuitry, or the like, that may perform various functions and operations, such as those described herein.

Access point 100 may comprise a device that connects to network 102 via any of a variety of connections, such as telephone dial-up, digital subscriber line (DSL), or cable modem connections. In other examples, access point 100 may be coupled to network 102 through different forms of connections, including wired or wireless connections. In some examples, access point 100 may be co-located with patient 14 and may comprise one or more programming units and/or computing devices (e.g., one or more monitoring units) that may perform various functions and operations described herein. For example, access point 100 may include a home-monitoring unit that is co-located with patient 14 and that may monitor the activity of LPD 16. In some examples, server 104 or computing devices 110 may control or perform any of the various functions or operations described herein, e.g., determine the attachment stability of LPD 16 based on one or more stability metrics.

In some cases, server 104 may be configured to provide a secure storage site for archival of stability metrics and/or transmitted attachment stability values that has been collected and generated from LPD 16 and/or programmer 20. Network 102 may comprise a local area network, wide area network, or global network, such as the Internet. In some cases, programmer 20 or server 104 may assemble stability information in web pages or other documents for viewing by and trained professionals, such as clinicians, via viewing terminals associated with computing devices 110. The system of FIG. 6 may be implemented, in some aspects, with general network technology and functionality similar to that provided by the Medtronic CareLink® Network developed by Medtronic, Inc., of Minneapolis, Minn.

In the manner of FIG. 6, computing device 110A or programmer 20, for example, may be remote computing devices that receive and present stability information transmitted from LPDs of multiple patients so that a clinician may prioritize the patients needing attention immediately. The computing device may use its communication module to receive the stability information (e.g., attachment stability values) transmitted from multiple LPDs via network 102.

Figure 7:
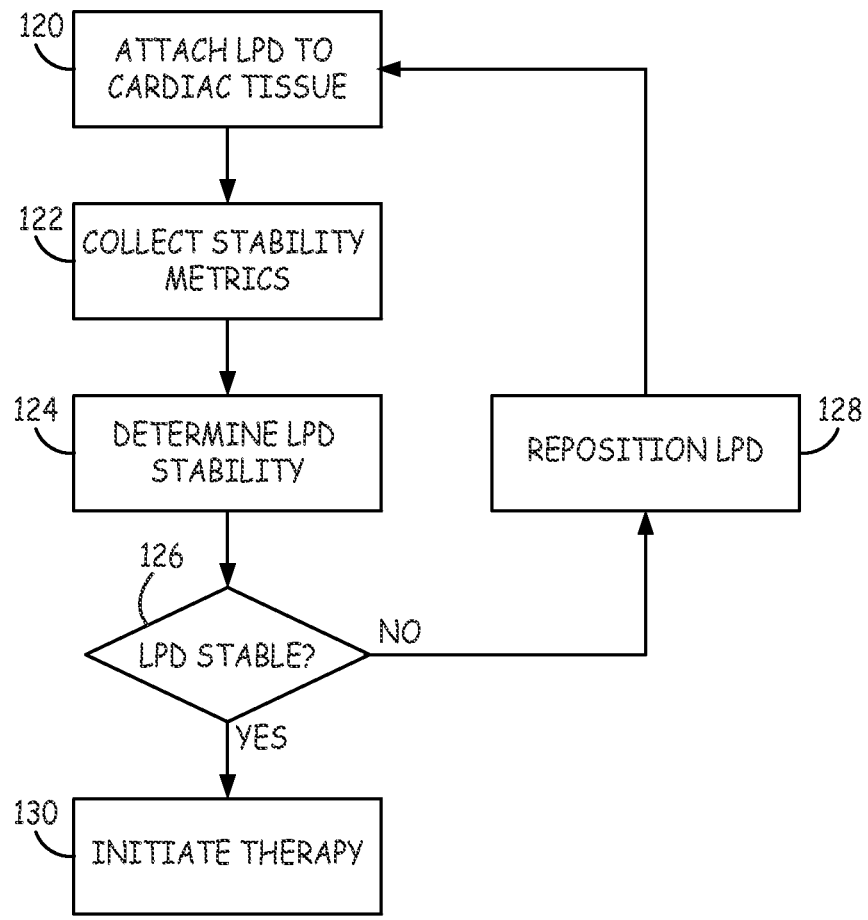
FIG. 7 is a flow diagram of an example technique for determining an attachment stability of an implanted LPD.

FIG. 7 is a flow diagram of an example technique for determining an attachment stability of LPD 16 during implantation. The clinician may initially insert LPD 16 into patient 14 and attach LPD 16 to cardiac tissue of heart 12 (120). For example, LPD 16 may be attached to a wall of right ventricle 18. Attachment of LPD 16 to cardiac tissue may include ensuring contact between electrode 34 and the tissue. The attachment of LPD 16 may also include tethering LPD 16 to tissue in addition to using fixation mechanisms 38.

Once LPD 16 is attached to cardiac tissue, LPD 16 may be instructed to collect stability metrics (122). LPD 16 may detect one or more stability metrics as desired by the clinician. From the detected stability metrics, LPD 16 may determine the attachment stability of LPD 16 (124). As described herein, the attachment stability may be based on one or more of the electrode impedance, capture threshold, cardiac events, sensing performance, and/or mechanical motion of LPD 16.

The mechanical motion of LPD 16 may be used with or without tension on LPD 16 from the tether.

As described herein, LPD 16 may wirelessly transmit stability information during implantation. In some examples, LPD 16 may be configured to measure one or more stability metrics while still attached to implantation tools used to deliver LPD 16 to the implantation site. If the attachment stability indicates that LPD 16 is not stable or attached appropriately to tissue ("NO" branch of block 126), then the clinician may remove or reposition LPD 16 (128). The clinician may then again attach LPD 16 to the desired tissue location. If the attachment stability indicates that LPD 16 is stable ("YES" branch of block 126), then the attachment if LPD 16 is complete and the clinician may begin to initiate therapy using LPD 16 (130).

Figure 8:
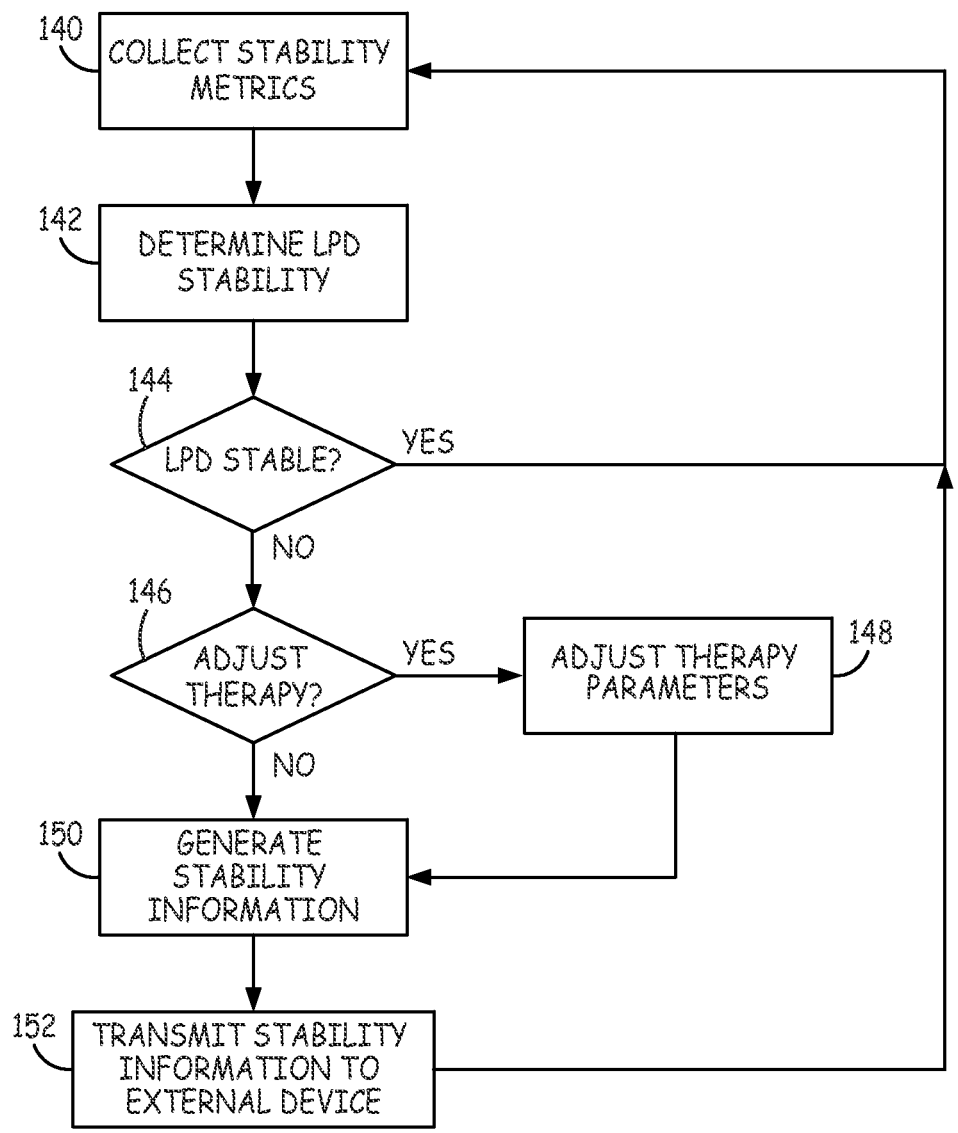
FIG. 8 is a flow diagram of an example technique for wirelessly transmitting stability information from an implanted LPD.

FIG. 8 is a flow diagram of an example technique for wirelessly transmitting stability information from LPD 16 when the LPD is implanted within patient 14. In the example of FIG. 8, stability information transmission may occur at a scheduled time, in response to a communication link between programmer 20, or in response to the attachment stability indicating at least partial dislodgement of LPD 16. Although programmer 20 will be described for the purposes of this example, any external computing device (e.g., a remote computing device) may be configured to communicate with LPD 16.

During monitoring and/or therapy, LPD 16 may collect stability metrics (140). LPD 16 may detect one or more stability metrics as desired by the clinician. From the detected stability metrics, LPD 16 may determine the attachment stability of LPD 16 (142). As described herein, the attachment stability may be based on one or more of the electrode impedance, capture threshold, cardiac events, sensing performance, and/or mechanical motion of LPD 16. As described herein, LPD 16 may compare each detected stability metric to a specific metric threshold. For example, the thresholds may be computed based on recently collected values or trends in each stability metric. In another example, LPD 16 may analyze the sensing rate or amplitude variability over time to detect any changes in LPD 16 operation. LPD 16 may also analyze electrogram morphology to identify evoked response anomalies of cardiac tissue that may be representative of dislodgement. In addition, or alternatively, activity sensor 64 may detect mechanical motion of LPD 16 within patient 14, patient posture, patient activity levels, or other movement related changes. LPD 16 may also determine its attachment stability by comparing two stability metrics to each other to look for cardiac event correlation.

If the determined attachment stability indicates that LPD 16 is attached and stable ("YES" branch of block 144), LPD 16 may continue to collect stability metrics (140). If the determined attachment stability indicates at least partial dislodgement of LPD 16 from tissue ("NO" branch of block 144), the LPD 16 determines if therapy needs to be adjusted, or if a therapy adjustment would be beneficial in view of the change in LDP stability (146). If the attachment stability indicates that pacing therapy parameters should be adjusted ("YES" branch of block 146), LPD 16 may automatically adjust one or more therapy parameters (148). Dislodgement of LPD 16 may indicate that electrode 34 is not fully capturing cardiac tissue. Therefore, LPD 16 may adjust a pulse amplitude, pulse width, or pulse frequency to attempt efficacious pacing despite dislodgement of LPD 16.

If no therapy adjustment is appropriate ("NO" branch of block 146) or therapy parameters have been adjusted (148), stability module 62 may generate stability information for transmission to programmer 20 (150). The stability information may include the attachment stability that indicates at least partial LPD dislodgement, or a severity of dislodgement. Once telemetry module 66 connects with programmer 20, telemetry module 66 may transmit the stability information to external programmer 20 (152). LPD 16 may then continue to collect stability metrics (140).

Although the transmission of stability information may generally be fully automated, the clinician may interact with LPD 16 in some examples to further investigate the presence or extent of LPD dislodgement. For example, the clinician may request additional patient metric data to confirm that dislodgement has occurred. In one example, the clinician may request that LPD 16 deliver specific stimulation pulses and record the evoked response from cardiac tissue that could indicate whether or not LPD 16 is dislodged. In other examples, the clinician may request more detailed patient metric data stored in memory 52 for further analysis. The clinician may utilize programmer 20 or a networked device to perform more complex analyses on the patient metric data to identify possible dislodgement problems. In this manner, LPD 16 may provide data as necessary to identify any problems with tissue/electrode interface problems and/or dislodgement of LPD 16 from tissue.

FIGS. 9A and 9B are example graphs of accelerations due to cardiac events and a patient walking, respectively. The acceleration data presented in FIGS. 9A and 9B is generated from a single axis accelerometer. However, similar data may be generated with multi-axis accelerometers and may be similarly interpreted. As shown in FIG. 9A, graph 160 provides an accelerometer signal 162 of cardiac events over time without any patient activity. Signal 162 is shown with an amplitude in g's (e.g., the acceleration due to earth's gravitation pull where 1 g equals approximately 9.8 meters/sec$^2$) with respect to time measured in seconds. The large magnitude spikes of signal 162 greater than 0.4 g's indicate heart wall contracts. Changes in the frequencies and/or magnitudes of signal 162 may be indicative of LPD 16 dislodgement.

As shown in FIG. 9B, graph 164 provides acceleration signal 166 generated from a patient walking at approximately 100 steps per minute without any cardiac event interference. Signal 166 is shown as an amplitude in g's with respect to time measured in seconds. Each large change in acceleration amplitude may be respective of a step of the patient during the activity. Relatively large changes in step magnitudes (e.g., greater than 20 percent of previous patient activity) and/or inconsistent steps may be representative of LPD 16 dislodgement.

Figure 10A:
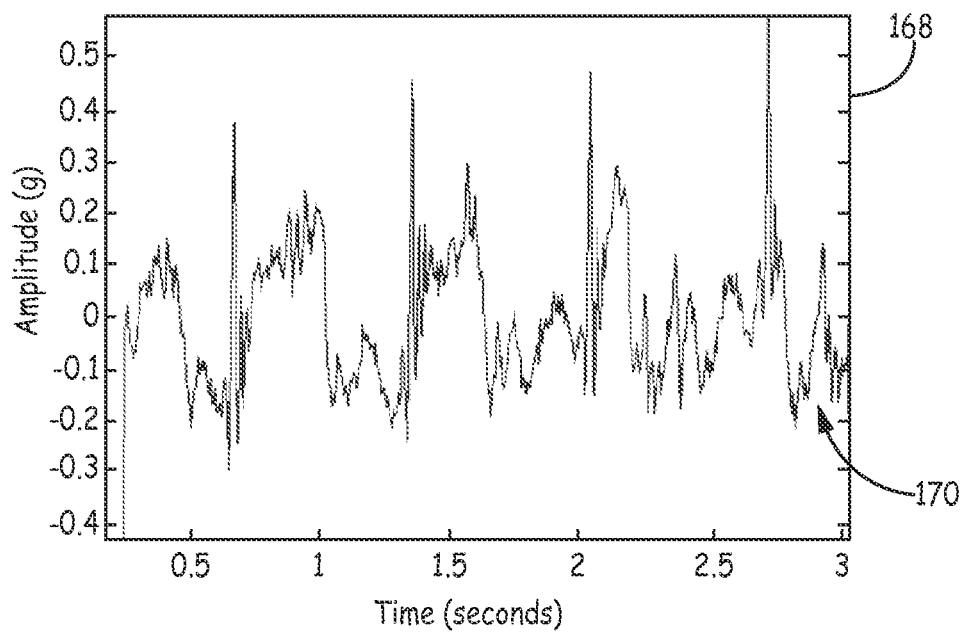
FIG. 10A is an example graph of merged accelerations due to both cardiac events and a patient walking.

FIG. 10A is an example graph of merged accelerations due to both cardiac events and a patient walking. As shown in FIG. 10A, graph 168 provides acceleration signal 170 that includes detected cardiac events when the patient is also involved in activity. It may be difficult to isolate cardiac events from patient activity without processing this signal to isolate the desired physiological action of the patient. As described above, LPD 16 may filter signal 170 to extract the orientation of LPD 16, patient activity, and/or cardiac events.

Figure 10B:
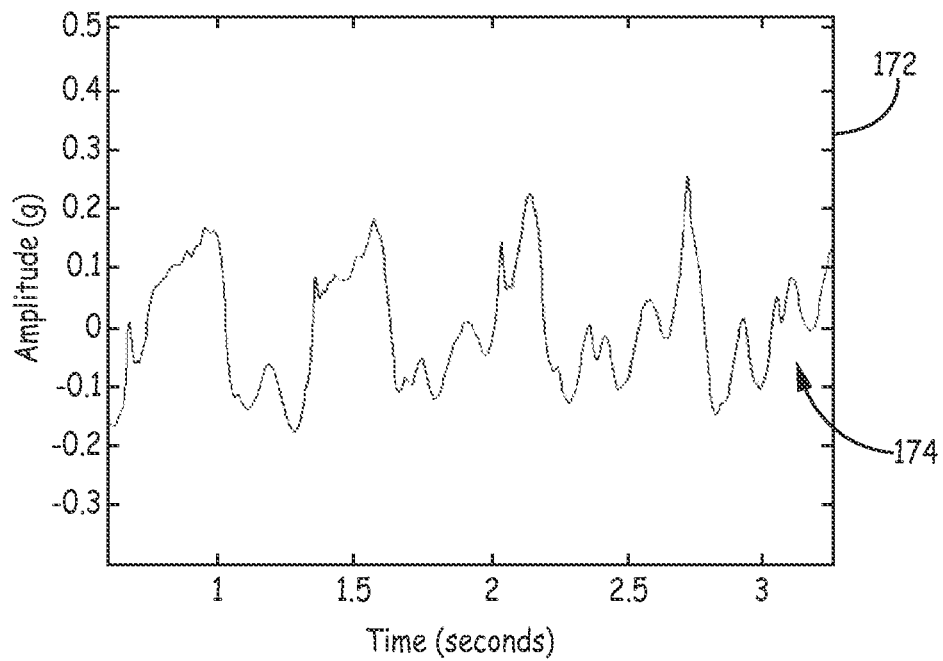
FIG. 10B is an example graph of filtered acceleration data from the merged accelerations of FIG. 10A.

FIG. 10B is an example graph of filtered acceleration data from the acceleration detected in graph 168 of FIG. 10A. As shown in FIG. 10B, graph 172 includes filtered signal 174. Filtered signal 174 may be generated from signal 170 of FIG. 10A by filtering accelerations greater than approximately 10 Hz from signal 170. Therefore, the remaining signal 174 includes acceleration frequencies associated with patient activity such as walking (e.g., frequencies greater than approximately 1 Hz and frequencies less than approximately 10 Hz). In other words, signal 174 may generally provide the accelerations associated with patient activity. Indeed, when compared to the patient activity provided by signal 166 of FIG. 9B, filtered signal 174 includes similar large changes in amplitude associated with waling steps as detected in the unfiltered signal 166. Therefore, signal 174 may be use as a patient metric for patient activity. Alternatively, signal 170 may be filtered to provide other patient metrics such as LPD 16 orientation (e.g., frequencies between approximately 0 Hz and 1 Hz) and cardiac events (e.g., frequencies between approximately 10 Hz and 250 Hz).

Figure 11A:
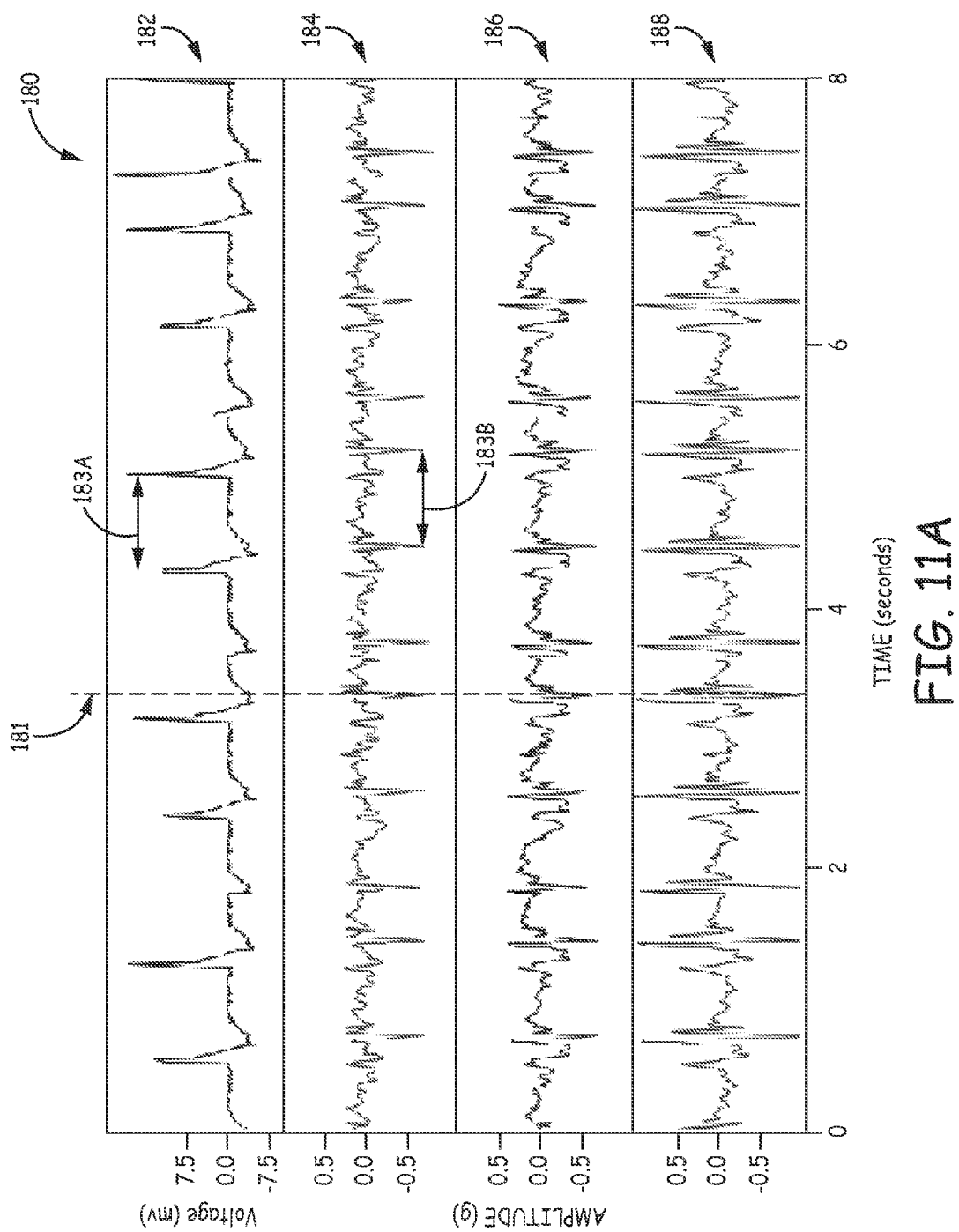
FIG. 11A is an example graph of electrocardiogram and accelerometer signals from an LPD fully attached within an atrium.
Figure 11B:
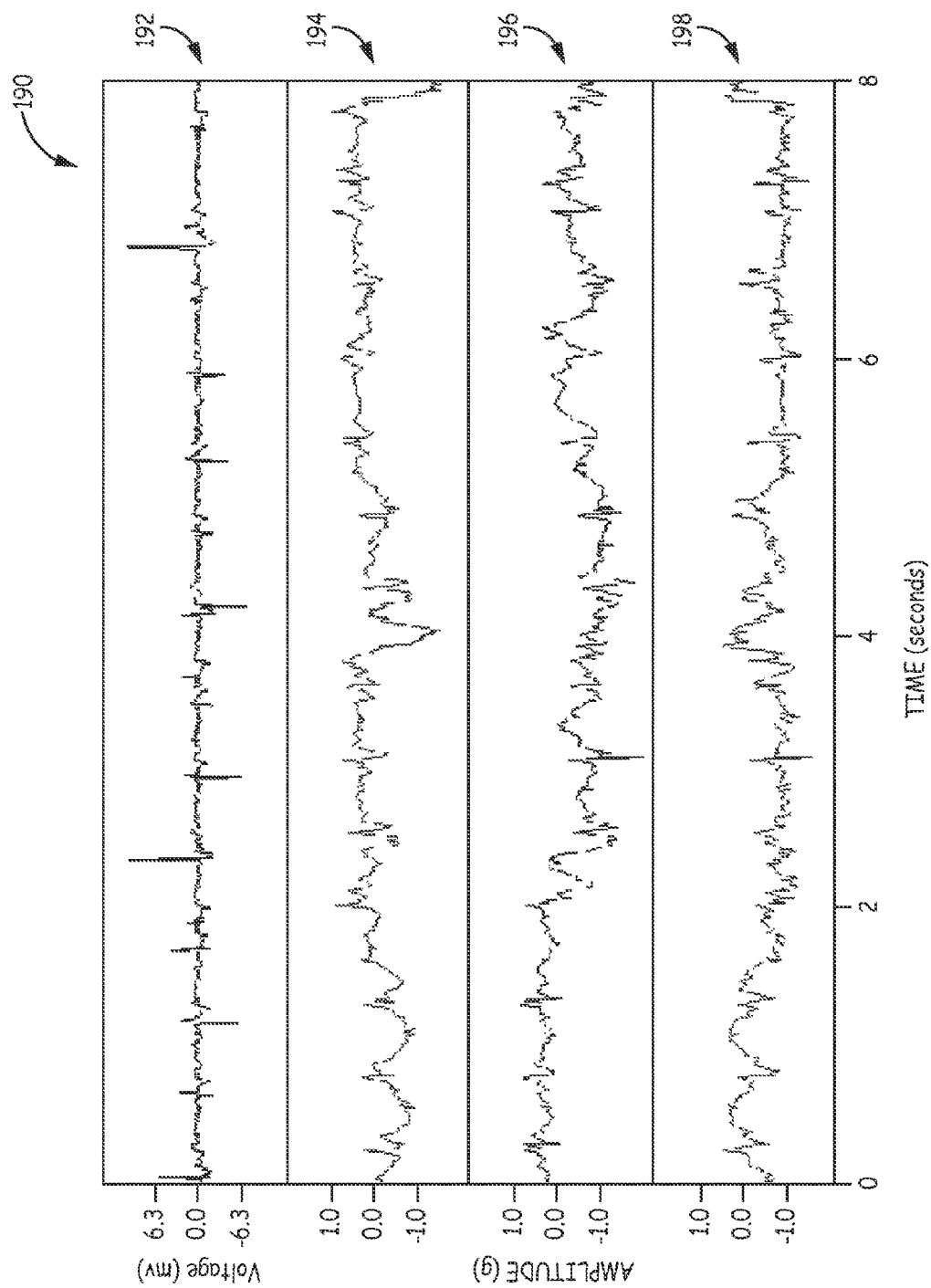
FIG. 11B is an example graph of electrocardiogram and accelerometer signals from an LDP at least partially dislodged within an atrium.

FIGS. 11A and 11B illustrate example differences in detectable signals between an LPD attached to cardiac tissue and an LPD at last partially dislodged from cardiac tissue. One or more stability metrics may be generated from these types of signals to differentiate between the scenarios where an LPD is fully attached to a chamber of the heart and the LPD becomes at least partially detached from the tissue of the heart. In the example of FIG. 11A, graph 180 illustrates time synchronized electrocardiogram signal 182 and accelerometer signals 184, 186, and 188 from an LPD fully attached within an atrium (e.g., right atrium 22).

Electrocardiogram signal 182 is a representation of the electrical signal detected by the LPD (e.g., between electrodes 34 and 36 of LPD 16) when the LPD is fully attached to an interior wall of the atrium. Electrocardiogram signal 182 is shown with an amplitude in millivolts (mV). Electrocardiogram signal 182 illustrates that when the LPD is fully attached to the cardiac tissue (e.g., the heart), signal capture may be sufficient to detect electrical events during the cardiac cycle. For example, large amplitude spikes may be representative of R-waves. Depending upon the vector used for generating electrogram signal 182, other electrical events such as P-waves and T-waves may also be detectable within electrogram signal 182.

Accelerometer signals 184, 186, and 188 are representations of the accelerations in respective vectors with respect to the patient. For example, an accelerometer may be a 3-axis accelerometer that outputs signals in three orthogonal directions. Each of accelerometer signals 184, 186, and 188 may thus represent the acceleration of the LPD in the respective axis or direction within the heart. Accelerometer signals 184, 186, and 188 are shown with amplitudes in g's, where one g equals the acceleration due to gravity (e.g., approximately 9.8 meters per second). The maximum amplitudes of each acceleration signal are at least partially dependent upon the orientation of the sensing vector with respect to wall motion. Since the axis of the vector for acceleration signal 188 may be oriented substantially parallel with the movement of the heart, signal 188 presents the largest acceleration amplitude of approximately 1.0 g's.

When the LPD is fully attached to the cardiac call, the output signals may correlate with each other and to detected cardiac events. As shown in FIG. 11A, higher amplitude events within each of accelerometer signals 184, 186, and 188 correlate with each other when the LPD is fully attached to the cardiac tissue. This mechanical motion correlation may indicate stability in the LPD. In addition, each of the respective signals 184, 186, and 188 may represent mechanical motion indicative of cardiac tissue movement. In other words, the mechanical motion may include high amplitude events at approximately a typical cardiac frequency range and/or at substantially consistent intervals. In other examples, acceleration signals greater than a predetermined threshold and/or acceleration signals with greater variation (e.g., high amplitude spikes between lower amplitude intervals) may indicate that the LPD is stable within the heart and fully attached to the tissue.

In addition, the capture threshold of electrocardiogram signal 182 during R-waves may be greater than a predetermined threshold to indicate that an electrode of the LPD is in contact with cardiac tissue. In another example, the cardiac waveform morphology of signal 182 may be representative of typical cardiac events. In other words, if R-waves, P-waves, and/or T-waves are detectable within the cardiac waveform morphology, the LPD may be sufficiently attached to the heart wall.

Furthermore, correlation between the electrocardiogram signal 182 and one or more of accelerometer signals 184, 186, and 188 may be used as a stability metric to differentiate between a fully attached LPD and an LPD that is partially or fully detached from the cardiac muscle. As shown in FIG. 11A, time reference 181 is used to illustrate that events detected in electrocardiogram signal 182 correlate with events detected in the accelerometer signals 184, 186, and 188. The inverted peak of signal 182 may refer to the S-wave that occurs at the same time as a spike in the acceleration detected by each of accelerometer signals 184, 186, and 188. The delay between the higher R-wave in signal 182 and the higher outputs of signals 184, 186, and 188 may be indicative of the mechanical delay between depolarization in the ventricles and the induced movement of the atrium in which the LPD is located.

The correlation between the electrocardiogram and accelerometer signals may also be present in the similar intervals between maximum peaks. Interval 183A may be representative of the R-R interval of a cardiac cycle. Interval 183B may be representative of the same R-R interval with a small time shift due to the mechanical delay between depolarization in the ventricles and tissue movement of the atrium. Although interval 183B is shown with respect to accelerometer signal 184, interval 183B may be calculated for any one or more of signals 184, 186, and 188. In this manner, a processor within the LPD or another device (e.g., an external programmer) may compare the mechanical motion of the LPD (e.g., the accelerometer signals) to one or more cardiac events (e.g., the electrocardiogram). The processor may be configured to determine that the LPD is fully attached to patient tissue when the mechanical motion correlates to one or more cardiac events.

In contrast to the example signals of FIG. 11A from a fully attached LPD, the example signals of FIG. 11B are obtained from an LPD that is dislodged or detached from the cardiac tissue. In the example of FIG. 11B, graph 190 illustrates time synchronized electrocardiogram signal 192 and accelerometer signals 194, 196, and 198 from an LPD that has become detached from the interior wall of an atrium (e.g., right atrium 22). An LPD that is still partially attached to the cardiac tissue may also produce signals similar to that of FIG. 11B.

Electrocardiogram signal 192 is a representation of the electrical signal detected by the LPD (e.g., between electrodes 34 and 36 of LPD 16) when the LPD is detached from an interior wall of the atrium. Electrocardiogram signal 192 is shown with an amplitude in millivolts (mV). Electrocardiogram signal 192 illustrates that when the LPD is not attached directly to the cardiac tissue (e.g., the heart), signal capture may be insufficient to completely detect electrical events during the cardiac cycle. For example, large amplitude spikes in signal 192, that may represent R-waves, are inconsistently spaced and of inconsistent amplitudes. Moreover, other electrical events such as P-waves and T-waves may be difficult to detect with smaller amplitudes and increased noise. With the LPD moving with respect to the heart in the detached condition, the sensing vector may be changing with respect to the heart to produce variable signals. The result may be similar to the example of electrocardiogram signal 192 with inconsistent intervals, amplitudes, and morphology.

Accelerometer signals 194, 196, and 198 are representations of the accelerations in respective vectors with respect to the patient. For example, an accelerometer may be a 3-axis accelerometer that outputs signals in three orthogonal directions. Each of accelerometer signals 194, 196, and 198 may thus represent the acceleration of the LPD in the respective axis or direction within the heart. Accelerometer signals 194, 196, and 198 are shown with amplitudes in g's, where one g equals the acceleration due to gravity (e.g., approximately 9.8 meters per second). Since the LPD is detached from the wall of the atrium, the amplitudes of signals 194, 196, and 198 may be reflective of fluid flow, intermittent contact with the atrium wall, and/or motions of the heart with respect to gravity.

In contrast to accelerometer signals 184, 186, and 188 of FIG. 11A, accelerometer signals 194, 196, and 198 illustrate a generally random and meandering amplitude over time. In other words, detachment from the heart wall means that the LPD is subject to movements and accelerations from multiple different forces instead of primarily the force from the chamber wall. In this manner, accelerometer signals 194, 196, and 198 do not correlate well with each other or to any detected cardiac events. This lack of any correlation (or a low level of correlation) in the mechanical motion of LPD may result in a calculated or determine stability metric indicative of instability or detachment of the LPD. Accelerometer signals 194, 196, and 198 may also provide a low correlation to cardiac events. The lack of high amplitude events a typical cardiac frequencies or any substantially consistent intervals between high amplitude events may indicate that the LPD is not attached to the chamber wall. In other examples, acceleration signals with amplitudes below a predetermined threshold may indicate that the detached LPD is no longer subject to accelerations from the chamber wall.

In addition, electrocardiogram signal 192 indicates that the LPD is not attached to the wall of the atrium. For example, the amplitudes of signal 192 are relatively low which may be below the capture threshold because there is no electrode in contact with the tissue of the chamber wall. In another example, the cardiac waveform morphology of signal 192 is not representative of typical cardiac events. In other words, R-waves, P-waves, and/or T-waves are not generally detectable within the cardiac waveform morphology. The LPD may thus not be sufficiently attached to the heart chamber wall.

Furthermore, correlation between the electrocardiogram signal 192 and one or more of accelerometer signals 194, 196, and 198 may be relatively low. This low correlation of electrocardiogram signals to accelerometer signals allows a processor to identify the detached LPD. As shown in graph 190, none of the cardiac events (e.g., higher amplitude waves) of electrocardiogram signal 192 correlate to higher amplitude events of any of accelerometer signals 194, 196, and 198. This lack of correlating signals indicates that LPD is not attached to the chamber wall. In another example, there is little to no correlation between any intervals present in electrocardiogram signal 192 and electrocardiogram signals 194, 196, and 198. Moreover, none of the signals of graph 190 indicate any cardiac related interval. In this manner, a processor within the LPD or another device (e.g., an external programmer) may compare the mechanical motion of the LPD (e.g., the accelerometer signals 194, 196, and 198) to one or more cardiac events (e.g., the electrocardiogram). The processor may be configured to determine that the LPD is fully attached to patient tissue when the mechanical motion correlates to one or more cardiac events. The processor may also be configured to indicate at least partial mechanical dislodgement of the LPD from patient tissue when the mechanical motion does not correlate to the one or more cardiac events. Any of these indicators or correlations may be used as a stability metric to indicate that LPD is not stable or attached to the chamber wall of the heart in the example of FIG. 11B.

The techniques described herein may provide timely information regarding the attachment or security of a leadless pacing device implanted within a chamber of the heart. Detachment or dislodgement of the LPD may reduce the ability of the LPD to deliver effective pacing therapy to the patient. More importantly, dislodgement of the LPD may result in adverse side effects from the LPD possibly interfering with valve operation, blood flow, or even downstream vasculature obstruction. Therefore, early detection of LPD dislodgement may reduce the amount of time for ineffective therapy, increase the likelihood of reattaching the LPD, and decrease adverse risks to the patient. The techniques for determining the attachment stability of the LPD may be varied based on location of the LPD implant, targeted therapy, patient specific conditions, and/or anticipated implant duration.

Various examples have been described for detecting stability metrics and determining an attachment stability of a leadless pacing device. The LPD may transmit this stability information to an external device to notify a clinician of LPD dislodgement or present data for further analysis. Any combination of detection and notification of attachment stability is contemplated. These and other examples are within the scope of the following claims.

The invention claimed is:

1. A method comprising:
   detecting two or more stability metrics with a leadless pacing device implanted within a patient; and
   determining an attachment stability of the leadless pacing device based on the two or more stability metrics;
   wherein determining the attachment stability comprises comparing two of the two or more stability metrics to each other, the method further comprising:
   comparing a mechanical motion of the leadless pacing device to one or more cardiac events; and
   determining the attachment stability to indicate at least partial mechanical dislodgement of the leadless pacing device from patient tissue when the mechanical motion does not correlate to the one or more cardiac events.

2. The method of claim 1, wherein determining the attachment stability comprises identifying at least one of an insufficient electrode/tissue interface for efficacious pacing therapy or an at least partial mechanical dislodgement of the leadless pacing device from patient tissue.

3. The method of claim 1, wherein the two or more stability metrics comprise at least one of an electrode impedance, a capture threshold, a cardiac waveform morphology, one or more cardiac events, a pacing threshold, oversensing, or a mechanical motion of the leadless pacing device.

4. The method of claim 1, wherein determining the attachment stability comprises comparing each of the two or more stability metrics to a respective specific metric threshold.

5. The method of claim 1, further comprising:
   generating stability information based on at least one of the two or more stability metrics and the attachment stability; and
   wirelessly transmitting stability information from the leadless pacing device to an external device.

6. The method of claim 5, further comprising automatically generating a stability notification and transmitting the stability notification to a clinician when the stability information indicates that at least one of pacing therapy is ineffective or the leadless pacing device is at risk for complete detachment from patient tissue.

7. The method of claim 1, wherein detecting two or more stability metrics with the leadless pacing device implanted within the patient comprises detecting two or more stability metrics with the leadless pacing device implanted completely within a heart of the patient.

8. A method comprising:
  detecting two or more stability metrics with a leadless pacing device implanted within a patient; and
  determining an attachment stability of the leadless pacing device based on the two or more stability metrics, wherein the two or more stability metrics comprise a primary stability metric and a secondary stability metric, and wherein determining the attachment stability comprises:
  detecting the primary stability metric;
  determining that the primary stability metric exceeds a respective specific metric threshold;
  in response to the determination, detecting the secondary stability metric; and
  comparing the secondary stability metric to the respective specific metric threshold.

9. A leadless pacing device comprising:
  two or more electrodes;
  a stability module configured to detect two or more stability metrics and determine an attachment stability of the device based on the two or more stability metrics; and
  a housing that encloses the stability module, wherein the two or more electrodes are disposed on the outside of the housing, wherein the stability module is configured to at least one of compare each of the two or more stability metrics to a respective specific metric threshold and compare two of the one or more stability metrics to each other, and wherein the stability module is configured to compare a mechanical motion of the leadless pacing device to one or more cardiac events and determine the attachment stability to indicate at least partial mechanical dislodgement of the device from patient tissue when the mechanical motion does not correlate to the one or more cardiac events.

10. The device of claim 9, wherein the stability module is configured to, based on the two or more stability metrics, identify at least one of an insufficient electrode/tissue interface for efficacious pacing therapy or an at least partial mechanical dislodgement of the device from patient tissue.

11. The device of claim 9, wherein the two or more stability metrics comprise at least one of an electrode impedance measured from one of the two or more leadless electrodes, a capture threshold of one of the two or more leadless electrodes, a cardiac waveform morphology generated from the two or more leadless electrodes, one or more cardiac events, a pacing threshold, oversensing, and a mechanical motion of the leadless pacing device.

12. The device of claim 9, further comprising an activity sensor configured to detect a mechanical motion of the device, wherein the activity sensor is contained within the housing.

13. The device of claim 9, further comprising a telemetry module configured to wirelessly transmit stability information to an external device, wherein the stability information is based on at least one of the two or more stability metrics and the attachment stability.

* * * * *